United States Patent
Thomas et al.

(10) Patent No.: US 10,555,890 B2
(45) Date of Patent: *Feb. 11, 2020

(54) FLEXIBLE SOLID COSMETIC COMPOSITION COMPRISING ANIONIC SURFACTANTS AND SOLID PARTICLES, AND COSMETIC TREATMENT PROCESS

(71) Applicant: L'OREAL, Paris (FR)

(72) Inventors: Beatrice Thomas, Deuil la Barre (FR); Damien Drillon, Paris (FR); Carine Pemosso, Paris (FR); Frederik Pinay, Saint Ouen l'Aumone (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/761,709

(22) PCT Filed: Jan. 20, 2014

(86) PCT No.: PCT/FR2014/050103
§ 371 (c)(1),
(2) Date: Jul. 17, 2015

(87) PCT Pub. No.: WO2014/111669
PCT Pub. Date: Jul. 24, 2014

(65) Prior Publication Data
US 2015/0359722 A1    Dec. 17, 2015

Related U.S. Application Data

(60) Provisional application No. 61/769,815, filed on Feb. 27, 2013.

(30) Foreign Application Priority Data

Jan. 18, 2013 (FR) ...................... 13 50443

(51) Int. Cl.
| | | |
|---|---|---|
| A61K 8/02 | (2006.01) |
| A61K 8/46 | (2006.01) |
| A61Q 5/12 | (2006.01) |
| A61Q 5/02 | (2006.01) |
| A61K 8/81 | (2006.01) |
| A61Q 5/00 | (2006.01) |

(52) U.S. Cl.
CPC .......... *A61K 8/8158* (2013.01); *A61K 8/0216* (2013.01); *A61K 8/0241* (2013.01); *A61K 8/466* (2013.01); *A61Q 5/006* (2013.01); *A61Q 5/02* (2013.01); *A61Q 5/12* (2013.01)

(58) Field of Classification Search
None
See application file for complete search history.

(56) References Cited

U.S. PATENT DOCUMENTS

| | | |
|---|---|---|
| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,961,347 A | 11/1960 | Floyd |
| 3,206,462 A | 9/1965 | McCarty |
| 3,227,615 A | 1/1966 | Korden |
| 3,236,733 A * | 2/1966 | Karsten ............... A61K 8/4933 424/DIG. 4 |
| 3,472,840 A | 10/1969 | Stone et al. |
| 3,589,978 A | 6/1971 | Kamal et al. |
| 3,632,559 A | 1/1972 | Matter et al. |
| 3,874,870 A | 4/1975 | Green et al. |
| 3,910,862 A | 10/1975 | Barabas et al. |
| 3,912,808 A | 10/1975 | Sokol |
| 3,929,990 A | 12/1975 | Green et al. |
| 3,966,904 A | 6/1976 | Green et al. |
| 3,986,825 A | 10/1976 | Sokol |
| 4,001,432 A | 1/1977 | Green et al. |
| 4,005,193 A | 1/1977 | Green et al. |
| 4,013,787 A | 3/1977 | Vanlerberghe et al. |

(Continued)

FOREIGN PATENT DOCUMENTS

| | | |
|---|---|---|
| CA | 1069522 A1 | 1/1980 |
| DE | 4402929 C1 | 6/1995 |

(Continued)

OTHER PUBLICATIONS

International Search Report for PCT/FR2014/050075, dated Oct. 29, 2014.
International Search Report for PCT/FR2014/050103, dated Oct. 28, 2014.
Todd, Charles, et al., "Volatile Silicone Fluids for Cosmetic Formulations," Cosmetics and Toiletries, vol. 91, Jan. 1976, pp. 29-32.
Brunauer et al., "Adsorption of Gases in Multimolecular Layers," Journal of the American Chemical Society, vol. 60, Feb. 1938, pp. 309-319.
Van De Hulst, H.C., "Light Scattering by Small Particles," Chapter 9, Wiley, N.Y., 1957.

(Continued)

*Primary Examiner* — H. Sarah Park
(74) *Attorney, Agent, or Firm* — The Marbury Law Group, PLLC

(57) ABSTRACT

The present invention relates to an aqueous cosmetic composition which is in the form of a flexible solid, comprising:
from 25% to 70% by weight of one or more anionic surfactants and
one or more types of non-hollow solid particles,
said composition comprising at least one anionic surfactant chosen from acylisethionates, preferably having an acyl group containing from 6 to 30 carbon atoms.
Said composition is of preferential use as a composition for cleaning or washing keratin materials, in particular the hair. The invention also relates to a cosmetic treatment process, in particular for caring for, cleaning and/or conditioning keratin materials, using said composition.

15 Claims, No Drawings

(56) References Cited

U.S. PATENT DOCUMENTS

| | | | |
|---|---|---|---|
| 4,025,617 A | 5/1977 | Green et al. | |
| 4,025,627 A | 5/1977 | Green et al. | |
| 4,025,653 A | 5/1977 | Green et al. | |
| 4,026,945 A | 5/1977 | Green et al. | |
| 4,027,008 A | 5/1977 | Sokol | |
| 4,027,020 A | 5/1977 | Green et al. | |
| 4,031,307 A | 6/1977 | DeMartino et al. | |
| 4,075,136 A | 2/1978 | Schaper | |
| 4,131,576 A | 12/1978 | Iovine et al. | |
| 4,137,180 A | 1/1979 | Naik et al. | |
| 4,165,367 A | 8/1979 | Chakrabarti | |
| 4,166,894 A | 9/1979 | Schaper | |
| 4,172,887 A | 10/1979 | Vanlerberghe et al. | |
| 4,189,468 A | 2/1980 | Vanlerberghe et al. | |
| 4,197,865 A | 4/1980 | Jacquet et al. | |
| 4,217,914 A | 8/1980 | Jacquet et al. | |
| 4,223,009 A | 9/1980 | Chakrabarti | |
| 4,240,450 A | 12/1980 | Grollier et al. | |
| 4,277,581 A | 7/1981 | Vanlerberghe et al. | |
| 4,348,202 A | 9/1982 | Grollier et al. | |
| 4,349,532 A | 9/1982 | Vanlerberghe et al. | |
| 4,381,919 A | 5/1983 | Jacquet et al. | |
| 4,422,853 A | 12/1983 | Jacquet et al. | |
| 4,445,521 A | 5/1984 | Grollier et al. | |
| 4,579,732 A | 4/1986 | Grollier et al. | |
| 4,591,610 A | 5/1986 | Grollier | |
| 4,608,250 A | 8/1986 | Jacquet et al. | |
| 4,719,099 A | 1/1988 | Grollier et al. | |
| 4,761,273 A | 8/1988 | Grollier et al. | |
| 4,777,040 A | 10/1988 | Grollier et al. | |
| 4,839,166 A | 6/1989 | Grollier et al. | |
| 4,874,554 A | 10/1989 | Lange et al. | |
| 4,948,579 A | 8/1990 | Jacquet et al. | |
| 4,970,066 A | 11/1990 | Grollier et al. | |
| 4,996,059 A | 2/1991 | Grollier et al. | |
| 5,009,880 A | 4/1991 | Grollier et al. | |
| 5,073,545 A | 12/1991 | Arima et al. | |
| 5,089,252 A | 2/1992 | Grollier et al. | |
| 5,196,189 A | 3/1993 | Jacquet et al. | |
| 5,230,007 A | 7/1993 | Baum | |
| 5,276,707 A | 1/1994 | Baum | |
| 5,372,751 A * | 12/1994 | Rys-Cicciari | A61K 8/44 510/130 |
| 5,616,746 A | 4/1997 | Mahieu et al. | |
| 5,618,523 A | 4/1997 | Zysman et al. | |
| 5,645,609 A | 7/1997 | Andrean et al. | |
| 5,665,778 A | 9/1997 | Semeria et al. | |
| 5,674,511 A * | 10/1997 | Kacher | A61K 8/375 424/401 |
| 5,703,026 A | 12/1997 | Setser et al. | |
| 5,728,389 A | 3/1998 | Sebillotte-Arnaud | |
| 5,773,611 A | 6/1998 | Zysman et al. | |
| 5,869,711 A | 2/1999 | Philippe et al. | |
| 5,958,392 A | 9/1999 | Grollier et al. | |
| 5,959,127 A | 9/1999 | Semeria et al. | |
| 6,001,376 A | 12/1999 | Mahieu et al. | |
| 6,039,963 A | 3/2000 | Philippe et al. | |
| 6,190,671 B1 | 2/2001 | Aubert et al. | |
| 6,210,691 B1 | 4/2001 | Mahieu et al. | |
| 6,245,343 B1 * | 6/2001 | Roulier | A61K 8/0208 424/401 |
| 7,470,725 B2 | 12/2008 | Schwertfeger et al. | |
| 2003/0199404 A1 | 10/2003 | Lorenzi et al. | |
| 2004/0097385 A1 | 5/2004 | Chen et al. | |
| 2004/0242097 A1 | 12/2004 | Hasenoehrl et al. | |
| 2005/0176615 A1 * | 8/2005 | Kinoshita | A61K 8/345 510/424 |
| 2009/0062406 A1 | 3/2009 | Loeffler | |
| 2015/0352027 A1 | 12/2015 | Thomas et al. | |

FOREIGN PATENT DOCUMENTS

| | | |
|---|---|---|
| DE | 4420736 C1 | 8/1995 |
| DE | 4424530 A1 | 1/1996 |
| DE | 4424533 A1 | 1/1996 |
| EP | 0078138 A2 | 5/1983 |
| EP | 0080976 A1 | 6/1983 |
| EP | 0122324 A1 | 10/1984 |
| EP | 0227994 A1 | 7/1987 |
| EP | 0337354 A1 | 4/1995 |
| EP | 0646572 A1 | 4/1995 |
| EP | 0692240 A1 | 1/1996 |
| EP | 0736522 A1 | 10/1996 |
| EP | 1106165 A1 | 6/2001 |
| EP | 1444975 A2 | 8/2004 |
| EP | 1516914 A1 | 3/2005 |
| FR | 1478523 A | 4/1967 |
| FR | 1492597 A | 8/1967 |
| FR | 1583363 A | 10/1969 |
| FR | 2077143 A | 10/1971 |
| FR | 2080759 A1 | 11/1971 |
| FR | 2162025 A1 | 7/1973 |
| FR | 2190406 A2 | 2/1974 |
| FR | 2270846 A1 | 12/1975 |
| FR | 2280361 A2 | 2/1976 |
| FR | 2316271 A1 | 1/1977 |
| FR | 2320330 A1 | 3/1977 |
| FR | 2336434 A1 | 7/1977 |
| FR | 2368508 A2 | 5/1978 |
| FR | 2383660 A1 | 10/1978 |
| FR | 2393573 A1 | 1/1979 |
| FR | 2413907 A1 | 8/1979 |
| FR | 2470596 A1 | 6/1981 |
| FR | 2505348 A1 | 11/1982 |
| FR | 2519863 A1 | 7/1983 |
| FR | 2542997 A1 | 9/1984 |
| FR | 2598611 A1 | 11/1987 |
| FR | 2673179 A1 | 8/1992 |
| FR | 2679771 A1 | 2/1993 |
| GB | 1546809 A | 5/1979 |
| GB | 2280906 A | 2/1995 |
| WO | 93/00741 A1 | 1/1993 |
| WO | 94/02158 A1 | 2/1994 |
| WO | 94/07844 A1 | 4/1994 |
| WO | 94/10131 A1 | 5/1994 |
| WO | 94/24097 A1 | 10/1994 |
| WO | 95/16665 A1 | 6/1995 |
| WO | 95/23807 A1 | 9/1995 |
| WO | 02/092051 A2 | 11/2002 |
| WO | 2014/111655 A2 | 7/2014 |

OTHER PUBLICATIONS

Van De Hulst, H.C., "Light Scattering by Small Particles," Chapter 10, Wiley, N.Y., 1957.
Wertz, et al., Essential Fatty Acids and Epidermal Integrity, Archive of Dermatology, vol. 123, Oct. 1987, pp. 1381-1384.
Bergey's Manual of Systemic Bacteriology, vol. 3, Section 23, 9th edition, 1989.
Non-Final Office Action for co-pending U.S. Appl. No. 14/761,705, dated Jul. 29, 2016.
Non-Final Office Action for copending U.S. Appl. No. 14/761,705, dated Sep. 21, 2017.
Final Office Action for copending U.S. Appl. No. 14/761,705, dated Jan. 30, 2017.
Final Office Action for co-pending U.S. Appl. No. 14/761,705, dated Jun. 10, 2019.
Non-Final Office Action for copending U.S. Appl. No. 14/761,705, dated Jan. 10, 2019.

* cited by examiner

FLEXIBLE SOLID COSMETIC COMPOSITION COMPRISING ANIONIC SURFACTANTS AND SOLID PARTICLES, AND COSMETIC TREATMENT PROCESS

CROSS REFERENCE TO RELATED APPLICATION

This is a national stage application of PCT/FR2014/050103, filed internationally on Jan. 20, 2014, which claims priority to U.S. Provisional Application No. 61/769,815, filed on Feb. 27, 2013; as well as French Application 1350443, filed on Jan. 18, 2013, all of which are incorporated herein by reference in their entireties.

The present invention relates to cosmetic compositions, in particular for cleaning or washing keratin materials, in particular the hair, which are in flexible solid form, and also to a cosmetic treatment method using same.

Many cosmetic washing products are known in the hair hygiene field. They are generally intended for cleaning keratin materials while at the same time providing them with good cosmetic properties (conditioning, hydration, softness, sheen, etc). Conventional products for cleaning keratin materials, such as shampoos, are usually in the form of liquids or creams which are more or less viscous.

However, these products are generally difficult to meter out; the more liquid they are, the greater their tendency to run through the fingers, making it difficult to meter them out and creating waste, and/or the greater their tendency to leak out of their packaging, which can be very bothersome when they come into contact with clothing, for example during moving.

In order to modify the texture, and in particular to make it more compact, conventional means consist in using thickeners, but this is often done to the detriment of the cosmetic effects of the composition. In addition, it has been noted that thicker compositions often have the drawback of requiring a lot of rinsing water in order to remove the surplus product on the hair. In many countries where access to water is restricted, the rinsing time and therefore the amount required to properly rinse-off the product are key indicators of the use qualities of a composition.

In order to overcome some of these problems, solid cosmetic formulations have been provided, but they generally have the drawback of being difficult to fractionate and/or to disintegrate on contact with water, making their use difficult and also requiring quite a large amount of water for optimum use. Moreover, the rapidity of the initiation of foaming is not optimal with these thick or solid compositions. Finally, these products do not always leave a clean natural feel to keratin materials, after removal of the water. In addition, users increasingly seek new textures and new concepts for products for washing keratin materials.

There is therefore a need to have compositions for washing keratin materials which do not run and which are more compact, modelable and economical. The compositions desired must be easy to apply to keratin materials, and must allow rapid initiation of foaming, i.e. the rapid obtaining of an appropriate and sufficiently abundant foam, when the composition is applied, generally by rubbing, to said keratin materials which have optionally been pre-wetted.

The objective of the present invention is to provide such compositions, which do not have the drawbacks of the prior art, and which are capable of rapidly enabling a foam appropriate for washing keratin materials to be obtained.

A subject of the invention is thus an aqueous cosmetic composition in flexible solid form, comprising:

from 25% to 70% by weight of one or more anionic surfactants, and
one or more types of full solid particles,
said composition comprising at least one anionic surfactant chosen from acyl isethionates, preferably having an acyl group comprising from 6 to 30 carbon atoms, better still from 12 to 24, even better still from 16 to 22 carbon atoms.

The composition according to the invention as an entirely unusual texture, which is non-tacky and relatively firm; it is simple to take, to handle and to apply; the composition is easy to grasp and does not run between the fingers. It can be very easily metered out and applied; it does not run and rinses off easily, while giving the keratin materials a natural and clean feel after removal.

In addition, the combination according to the invention makes it possible to obtain a flexible solid texture variety, without the addition of thickener; the distribution of the composition on the keratin materials is improved, and the rapidity of initiation of foaming and the rinsing time are also improved.

Preferentially, the composition according to the invention is non-coloring.

According to the present invention, the term "non-coloring composition" is intended to mean a composition not containing any dye for keratin fibers such as direct dyes or oxidation dye precursors (bases and couplers). If they are present, their content does not exceed 0.005% by weight, relative to the total weight of the composition. Specifically, at such a content, only the composition would be dyed, i.e. no dyeing effect would be observed on the keratin fibers.

Advantageously, the composition according to the invention is a foaming composition.

The composition according to the invention is therefore in flexible solid form. The term "flexible solid" is intended to mean in particular the fact that the composition does not flow under its own weight, but it can be deformed by pressure, for example with a finger; its consistency is similar to that of a butter (without the fatty nature of course), malleable and graspable. The composition can be easily modeled in the hand; it can also be easily broken in the hand in order to take only the required amount of product. In particular, this composition can be packaged in single-dose form, for example in the form of sachets.

Preferably, the flexible solid composition according to the invention meets at least one of the physicochemical criteria hereinafter, in particular at least two criteria, preferentially the three criteria.

Unless otherwise indicated, these criteria are measured at ambient temperature (25° C.) and atmospheric pressure (1 atm), the composition having undergone centrifugation for 15 minutes at 10 kg in order to remove the bubbles for the evaluation of criteria 1 and 2.

Criterion 1: the composition according to the invention has a viscoelastic spectrum at 25° C., measured between $10^{-2}$ Hz and 100 Hz, such that there is no crossover point between the curves G' and G", G' always being strictly greater than G" (for measurements carried out at a frequency of between $10^{-2}$ Hz and 100 Hz).

The viscoelastic spectrum is established using a Thermo Haake RS600 imposed-stress rheometer in cone-plate geometry. The temperature was regulated by a Peltier-effect plane and an anti-evaporation device (solvent trap filled with water for the measurements at 25° C.).

Measurements were carried out with oscillation between $10^{-2}$ Hz and 100 Hz, at a stress of 0.03% with a sanded C60 1°/Ti cone and/or at a stress of 0.05% with a sanded C35 2/Ti cone.

G', which corresponds to the storage modulus reflecting the elastic response and the solid nature of the sample, is measured; G", which corresponds to the loss modulus reflecting the viscous response and the liquid nature of the sample, is also measured.

Criterion 2: the composition according to the invention is such that it has a threshold stress at 25° C. greater than or equal to 100 Pa.

The threshold stress is determined by scanning under stress at 25° C. An imposed-stress Thermo Haake RS600 rheometer with sanded cone-plate geometry is used.

The temperature was regulated by a Peltier-effect plane and an anti-evaporation device (solvent trap filled with water for the measurements at 25° C.).

A logarithmic stress ramp from 0.1 to 250 Pa is performed over a period of 2 minutes. Two adjustment lines corresponding to the stationary regimes (solid and liquid behaviors) are plotted on the curve representing the strain as a function of the stress (logarithmic coordinates). The intersection of these two lines gives the value sought.

The composition according to the invention is such that it has a threshold stress greater than or equal to 100 Pa, preferably ranging from 100 to 900 Pa, at 25° C.

Criterion 3: the composition according to the invention is such that it has a penetration force at 25° C. greater than or equal to 210 g.

The penetration force is determined by penetrometry, with a tip having a diameter of 1.5 cm and at a speed of 10 mm/s. The texture analysis measurements are carried out at 25° C. using a Stable Micro Systems TA.XT Plus texture analyzer. The penetrometry experiments are carried out with a metal rod which has a Delrin screw tip, 15 mm in diameter and 6 mm high, connected to the measuring head. The piston pushes into the sample at a constant speed of 10 mm/s, to a height of 15 mm or 20 mm depending on the height of product in the pot (of diameter 90 mm, and height 30 mm, made of plastic). The force exerted on the piston is recorded and the average value of the force is calculated.

The composition according to the invention is such that it has a penetration force at 25° C. greater than or equal to 210 g, preferably ranging from 210 to 900 g, better still ranging from 350 to 800 g.

Preferably, the composition according to the invention is such that it has a threshold stress at 25° C. greater than or equal to 100 Pa, preferably ranging from 100 to 900 Pa; and/or is such that it has a penetration force at 25° C. greater than or equal to 210 g, preferably ranging from 210 to 900 g, better still ranging from 350 to 800 g.

Even better still, the composition according to the invention is such that it has a threshold stress at 25° C. greater than or equal to 100 Pa, preferably ranging from 100 to 900 Pa; and a penetration force at 25° C. greater than or equal to 210 g, preferably ranging from 210 to 900 g, better still ranging from 350 to 800 g.

In the present description, the term "at least one" is equivalent to the expression "one or more", and the term "between . . . and . . . " is equivalent to the term "ranging from . . . to . . . ", which implies that the limits are included.

Anionic Surfactants

The composition according to the invention comprises at least one anionic surfactant chosen from acyl isethionates having an acyl group preferably comprising from 6 to 30 carbon atoms, better still from 12 to 24, even better still from 16 to 22 carbon atoms.

They preferably correspond to the following formula: R—C(O)—O—CH$_2$CH$_2$SO$_3$M, in which R—C(O) is an acyl group preferably comprising from 6 to 30 carbon atoms, better still from 12 to 24, even better still from 16 to 22 carbon atoms, and M denotes a cosmetically acceptable counterion.

A mixture of anionic surfactants chosen from acyl isethionates can quite obviously be used.

Preferably, the composition according to the invention comprises one or more anionic surfactants chosen from cocoyl isethionates and/or lauroyl isethionates.

The salified forms are in particular alkali metal salts such as sodium salts, ammonium salts, amine salts, amino alcohol salts or alkaline-earth metal salts, for example magnesium salts. Alkali metal or alkaline-earth metal salts and in particular the sodium or magnesium salts are preferably used.

The composition according to the invention may also comprise one or more additional anionic surfactants.

The term "anionic surfactant" is intended to mean a surfactant comprising, as ionic or ionizable groups, only anionic groups. These anionic groups are preferably chosen from the $CO_2H$, $CO_2^-$, $SO_3H$, $SO_3^-$, $OSO_3H$, $OSO_3^-$, $—H_2PO_3$, $—HPO_3^-$, $—PO_3^{2-}$, $—H_2PO_2$, $=HPO_2$, $—HPO_2^-$, $=PO_2^-$, $=POH$ or $=PO^-$ groups. The additional anionic surfactants may be oxyalkylenated and then preferably comprise from 1 to 50 ethylene oxide units and better still from 1 to 10 ethylene oxide units.

Preferably, the additional anionic surfactants are chosen from sulfate, sulfonate or carboxylate anionic surfactants, preferentially from sulfonate anionic surfactants and carboxylate anionic surfactants. In one preferred embodiment, the composition does not comprise any additional surfactants, or, if it does comprise them, it does not comprise any additional sulfate anionic surfactants (comprising a sulfate group).

According to the invention, included in the sulfonate anionic surfactants are sulfonate anionic surfactants without a carboxylate group; and included in the carboxylate anionic surfactants are carboxylate anionic surfactants which can optionally also comprise a sulfate or sulfonate group, for example.

The sulfate or sulfonate anionic surfactants without a carboxylic group that can be used in the composition according to the invention as additional anionic surfactants can be chosen in particular from alkyl sulfates, alkyl ether sulfates, alkylamido ether sulfates, alkylaryl polyether sulfates, monoglyceride sulfates, alkylsulfonates, alkylamidesulfonates, alkylarylsulfonates, alpha-olefin sulfonates, paraffin sulfonates, N-acyltaurates, N-methyl-N-acyltaurates, and the corresponding acid forms, the alkyl and acyl groups of all these compounds preferably comprising from 6 to 30 carbon atoms, better still from 12 to 24, or even from 16 to 22 carbon atoms, and the aryl group preferably denoting a phenyl or benzyl group.

The carboxylate anionic surfactants that may be used in the composition according to the invention as additional anionic surfactants can be chosen from alkyl sulfosuccinates, alkyl ether sulfosuccinates, alkylamide sulfosuccinates, acyl glycinates, acylsarcosinates and acyl glutamates, and the corresponding acid forms, the alkyl and/or acyl groups of these compounds comprising from 6 to 30 carbon atoms, better still from 12 to 24, or even from 16 to 22 carbon atoms.

Use may also be made of alkyl monoesters of polyglycoside-polycarboxylic acids such as alkyl polyglycoside citrates, alkyl polyglycoside tartrates and alkyl polyglycoside sulfosuccinates, and alkylsulfosuccinamates, the alkyl or acyl group of these compounds comprising from 6 to 30 carbon atoms, better still from 12 to 24, or even from 16 to 22 carbon atoms; use may also be made of the salts thereof.

Use may also be made of acyllactylates, the acyl group of which comprises from 6 to 30 carbon atoms, better still from 8 to 20 carbon atoms, or even from 12 to 24 carbon atoms.

Mention may also be made of alkyl-D-galactosideuronic, polyoxyalkylenated ($C_{14}$-$C_{30}$)alkyl ether carboxylic acids, polyoxyalkylenated ($C_{14}$-$C_{30}$)alkyl($C_6$-$C_{30}$)aryl ether carboxylic acids, polyoxyalkylenated ($C_{14}$-$C_{30}$)alkylamido ether carboxylic acids; and also the salts of all these compounds; preferably the compounds comprising from 2 to 50 ethylene oxide units; and also mixtures thereof.

Preferably, the composition comprises one or more additional anionic surfactants chosen from:
- $C_6$-$C_{24}$ and in particular $C_{12}$-$C_{20}$ alkyl sulfates;
- $C_6$-$C_{24}$ and in particular $C_{12}$-$C_{20}$ alkyl ether sulfates; preferably comprising from 2 to 20 ethylene oxide units;
- $C_6$-$C_{24}$ and in particular $C_{12}$-$C_{20}$ acyl glutamates; in particular stearoyl glutamates;
- $C_6$-$C_{24}$ and in particular $C_{12}$-$C_{20}$ acyl sarcosinates; in particular palmitoyl sarcosinates;
- $C_6$-$C_{24}$ and in particular $C_{12}$-$C_{20}$ acyl lactylates; in particular behenoyl lactylates;
- ($C_6$-$C_{24}$)alkyl ether carboxylates, preferably ($C_{12}$-$C_{20}$) alkyl ether carboxylates;
- $C_6$-$C_{24}$ and in particular $C_{12}$-$C_{20}$ alkylsulfosuccinates, in particular laurylsulfosuccinates.

The salified forms are in particular alkali metal salts such as sodium salts, ammonium salts, amine salts, amino alcohol salts or alkaline-earth metal salts, for example magnesium salts. Alkali metal or alkaline-earth metal salts and in particular the sodium or magnesium salts are preferably used.

Preferentially, the composition according to the invention comprises one or more anionic surfactants chosen from the acyl isethionates defined above, combined with one or more surfactants chosen from $C_6$-$C_{24}$ and in particular $C_{12}$-$C_{20}$ alkylsulfosuccinates.

Preferably, the total amount of anionic surfactant(s) in the composition according to the invention ranges from 25% to 65% by weight, or even from 30% to 60% by weight, relative to the total weight of the composition.

Preferably, the total amount of anionic surfactant(s), chosen from sulfonate anionic surfactants and carboxylate anionic surfactants, in the composition of the invention ranges from 20% to 60% by weight, preferentially from 25% to 50% by weight, relative to the total weight of the composition.

Preferably, the total amount of acyl isethionates in the composition according to the invention ranges from 12% to 50% by weight, better still from 15% to 40% by weight, even better still from 20% to 35% by weight relative to the total weight of the composition.

Full Solid Particles

The composition according to the invention comprises at least one type of full solid particles, which are preferably insoluble in said composition; it can quite obviously comprise several different types of full solid particles.

Said solid particles are generally water-insoluble. For the purposes of the present invention, the term "water-insoluble" is intended to mean a composition of which the solubility in water at 25° C. and at atmospheric pressure is less than 0.1%, better still less than 0.001% by weight.

The term "full particles" is intended to mean particles which are not hollow, i.e. different than particles comprising at least one continuous shell (or a superficial layer) and at least one central cavity.

Advantageously, the particles according to the invention have a number-average primary size ranging from 0.001 to 1000 μm, preferably from 0.01 to 700 μm, preferentially from 0.5 to 200 μm.

For the purposes of the present invention, the term "primary particle size" is intended to mean the maximum dimension that it is possible to measure between two diametrically opposite points on an individual particle. The size of the particles may be determined by transmission electron microscopy or by measuring the specific surface area via the BET method or by laser particle size analysis.

The particles used in the composition according to the invention may have different shapes, for example may be sphere-shaped, flake-shaped, needle-shaped or platelet-shaped, and preferably they are approximately spherical.

The composition according to the invention preferably comprises particles of one or more organic compounds, which may be natural or synthetic, generally polymer compounds, and/or particles of one or more inorganic compounds.

The particles of natural organic compounds may in particular be micronized fruit kernels.

The particles of non-polymer synthetic organic compounds may in particular be chosen from pyridinethione salts, in particular the calcium, magnesium, barium, strontium, zinc, cadmium, tin and zirconium salts. The zinc salt of pyridinethione is particularly preferred. A zinc salt of pyridinethione is sold in particular under the name Omadine zinc by the company Arch Personal Care.

The particles of polymer organic compounds may be particles of crosslinked or non-crosslinked polymers.

These polymers are preferably in the vitreous state, i.e. they have a glass transition temperature significantly higher than ambient temperature or the temperature at which they are used (for example the temperature of the human body).

The particles of one or more organic compounds that may be used in the cosmetic composition according to invention may in particular be chosen from polyamide powders; powders of acrylic polymers, in particular of crosslinked poly(sodium acrylate), or of poly(methyl methacrylate); powders of acrylic copolymers, in particular of poly(methyl methacrylate)/ethylene glycol dimethacrylate, of poly(allyl methacrylate)/ethylene glycol dimethacrylate, of ethylene glycol dimethacrylatel/lauryl methacrylate copolymer, or of polyacrylate/alkyl acrylate; polystyrene powders; polyethylene powders, in particular polyethylene/acrylic acid powders; and silicone resin microbeads.

Mention may be more particularly made, as particles of organic compounds according to the invention, of:
- polyamide (Nylon®) powders, for example those sold under the names Orgasol® 4000 and Orgasol® 2002 UD NAT COS 204 by the company Atochem,
- powders of acrylic polymers, in particular of crosslinked poly(sodium acrylate), for instance those sold under the name ASAP 2000 by the company Chemoal or Hysorb M7055 for the company BASF, or of poly(methyl methacrylate), for instance those sold under the name Covabead® LH85 or Covabead® PMMA by the company Sensient or those sold under the name Micropearl® MHB, Micropearl® M 100 or Micropearl® M 310 by the company Matsumoto, powders of acrylic copolymers, in particular of poly (methyl methacrylate)/ethylene glycol dimethacrylate, such as those sold under the name Dow Corning 5640 Microsponge® Skin Oil Adsorber by the company Dow Corning, or those sold under the name Ganzpearl® GMP-0800 by the company Aica Kogyo, of poly(allyl methacrylate)/ethylene glycol dimethacrylate, such as those sold under the name Polypore® L200 or Polypore® E200 by the company Amcol, of ethylene glycol dimethacrylate/lauryl methacrylate copolymer, such as those sold as Polytrap® 6603 by the company Dow Corning, or of polyacrylate/ethylhexyl acrylate, such as those sold under the name Techpolymer® ACX 806C by the company Sekisui, polystyrene powders, such as those sold under the name Polysphere 3 000 SP by the company Presperese, polystyrene/divinylbenzene powders, such as those sold under the name Techpolymer® SBX8 by the company Sekisui, styrene/acrylate copolymer powders, such as those sold under the name Sunspheres Powder by the company Rohm & Haas, polyethylene powders, in particular polyethylene/acrylic acid powders sold under the name Flobeads® by the company Sumitomo, or polyethylene beads sold under the name Micropoly 220 L by the company Micro Powders, silicone resin microbeads, such as those sold under the name Tospearl® by the company Toshiba Silicone, in particular Tospearl® 240A and Tospearl® 120A. Preferably, the particles of organic compounds (or organic particles) are chosen from polyamide powders, powders of crosslinked poly(sodium acrylate), polyethylene powders and poly(methyl methacrylate) powders.

Said organic particles may be optionally surface-treated with a hydrophobic treating agent. Thus, the organic particles may be made hydrophobic by chemical coating or grafting with products such as: silicones, such as methicones or dimethicones; amino acids, N-acyl amino acids or salts thereof; metal soaps, such as aluminum dimyristate, the aluminum salt of hydrogenated tallow glutamate; fluorinated derivatives, for instance perfluoroalkyl phosphates, perfluoroalkylsilanes, poly(hexafluoropropylene oxide)s, polyorganosiloxanes comprising perfluoroalkyl groups, perfluoropolyethers; lecithin, isopropyl triisostearoyl titanate; fatty acids such as stearic acid.

The term "alkyl" mentioned in the compounds cited above may in particular denote a linear, branched or cyclic alkyl group containing from 1 to 30 carbon atoms, in particular from 5 to 16 carbon atoms.

The N-acyl amino acids can comprise an acyl group comprising from 8 to 22 carbon atoms, such as, for example, a 2-ethylhexanoyl, caproyl, lauroyl, myristoyl, palmitoyl, stearoyl or cocoyl group.

The salts of these compounds may be the aluminum, magnesium, calcium, zirconium, zinc, sodium or potassium salts.

The amino acid may be, for example, lysine, glutamic acid or alanine.

By way of example, mention may be made of the poly (methyl methacrylate) microspheres coated with isopropyl triisostearyl titanate, having a size of 2-15 μm, sold by the company Kobo under the reference BPA-515.

The particles of one or more inorganic compounds (or inorganic particles) that may be used in the cosmetic composition according to the invention can be chosen from metal particles, oxides, inorganic salts, carbides, nitrides, borides, sulfides and hydroxides.

The term "metal particles" is intended to mean particles formed by metals, in particular chosen from alkaline-earth metals, transition metals, rare earth metals, and alloys of these metals.

Preferably, the metals used are boron, aluminum, copper, cadmium, selenium, silver, gold, indium, iron, platinum, nickel, molybdenum, silicon, titanium, tungsten, antimony, palladium, zinc, tin, and alloys of these metals. Among these metals, gold, silver, platinum, cadmium, selenium, and alloys of these metals are quite particularly preferred.

Among these compounds, mention may be made in particular of selenium disulfide.

The particles of one or more inorganic compounds may also be oxides. Mention may be made of the oxides of the elements of columns 1 to 14 of the periodic table of elements. In particular, mention may in particular be made of titanium oxide, zinc oxide, cerium oxide, zirconium oxide, aluminum oxide and bismuth oxychloride. Among these compounds, zinc oxide is quite particularly preferred. The particles of one or more inorganic compounds may be inorganic salts. Mention may in particular be made of barium sulfate, calcium carbonate, calcium sulfate, calcium phosphate and magnesium hydrogen carbonate.

Among these compounds, calcium carbonate is preferred.

Among the particles of one or more inorganic compounds belonging to the species described above, mention may also be made of clays, silicates, alumina, silica, kaolin and hydroxyapatite.

In particular, the silicas that can be used may be natural and untreated. Mention may thus be made of the silicas provided under the names Sillitin N85, Sillitin N87, Sillitin N82, Sillitin V85 and Sillitin V88 by the company Hoffman Mineral, or Sunsil 130 by the company Sunjin Chemical, MSS-500-3 H by the company Kobo, Sunsphere H 51 by the company AGC SI-Tech, and the hollow particles of amorphous silica of ellipsoidal shape sold by Kobo under the reference silica shells. They may be fumed silicas. The fumed silicas may be obtained by high-temperature hydrolysis of a volatile silicon compound in an oxyhydrogen flame, producing a finely divided silica. This process makes it possible in particular to obtain hydrophilic silicas which bear a large number of silanol groups at their surface.

It is possible to chemically modify the surface of said silica via a chemical reaction which brings about a reduction in the number of silanol groups. It is possible in particular to replace silanol groups with hydrophobic groups: a hydrophobic silica is then obtained. The hydrophobic groups may be:

(a) trimethylsiloxyl groups, which are obtained in particular by treating fumed silica in the presence of hexamethyldisilazane. Silicas thus treated are known as Silica silylate according to the CTFA (6th Edition, 1995).

(b) dimethylsilyloxyl or polydimethylsiloxane groups, which are obtained in particular by treating fumed silica in the presence of polydimethylsiloxane or dimethyldichlorosilane. Silicas thus treated are known as silica dimethyl silylate according to the CTFA (6th Edition, 1995).

In particular, among the hydrophobic silicas, mention may be made of silica aerogels. Aerogels are ultra-light porous materials, the first ones of which were made by Kristler in 1932. They are generally synthesized via a sol-gel process in liquid medium and then dried by extraction of a supercritical fluid. The supercritical fluid most commonly used is supercritical $CO_2$. This type of drying makes it possible to avoid shrinkage of the pores and of the material.

Other types of drying also make it possible to obtain porous materials from gel, namely (i) drying by cryodesiccation, which consists in solidifying the gel at low temperature and then in sublimating off the solvent, and (ii) drying by evaporation. The materials thus obtained are then known, respectively, as cryogels and xerogels. The sol-gel process and the various drying operations are described in detail in Brinker C J., and Scherer G. W., Sol-Gel Science, New York: Academic Press, 1990.

The term "hydrophobic silica" is intended to mean any silica of which the surface is treated with silylating agents, for example halogenated silanes such as alkylchlorosilanes, siloxanes, in particular dimethylsiloxanes such as hexamethyldisiloxane, or silazanes, so as to functionalize the OH groups with silyl groups Si—Rn, for example trimethylsilyl groups.

Preferably, the hydrophobic aerogel particles which can be used in the present invention advantageously have a specific surface area per unit of mass (SM) ranging from 500 to 1500 $m^2/g$, preferably from 600 to 1200 $m^2/g$ and better still from 600 to 800 $m^2/g$ and/or have an oil absorption capacity measured at the wet point ranging from 5 to 18 ml/g of particles, preferably from 6 to 15 ml/g and better still from 8 to 12 ml/g.

The absorption capacity measured at the wet point, denoted Wp, corresponds to the amount of oil which it is necessary to add to 100 g of particles in order to obtain a homogeneous paste. It is measured according to the "wet point" method or the method for determining the oil uptake of a powder according to the principle described in standard NF T 30-022. It corresponds to the amount of oil adsorbed on the available surface of the powder and/or absorbed by the powder by virtue of the wet point measurement, described below: an amount m=2 g of powder is placed on a glass plate and then the oil (isononyl isononanoate) is added dropwise. After addition of 4 to 5 drops of oil to the powder, mixing is carried out using a spatula, and addition of oil is continued until conglomerates of oil and powder have formed. From this point, the oil is added at the rate of one drop at a time and the mixture is subsequently triturated with the spatula. The addition of oil is stopped when a firm, smooth paste is obtained. This paste must be able to be spread on the glass plate without cracking or forming lumps. The volume Vs (expressed in ml) of oil used is then noted. The oil uptake corresponds to the ratio Vs/m.

The hydrophobic silica aerogel particles used according to the present invention are preferably silylated silica (INCI name: silica silylate) aerogel particles.

The preparation of hydrophobic silica aerogel particles that have been surface-modified by silylation is described earlier in U.S. Pat. No. 7,470,725. Use will be made in particular of aerogel particles of hydrophobic silica surface-modified with trimethylsilyl groups.

The hydrophobic aerogel particles that may be used in the present invention advantageously have a size, expressed as the mean diameter (D[0.5]), of less than 1500 μm, and preferably ranging from 1 to 30 μm, preferably from 5 to 25 μm, better still from 5 to 20 μm and even better still from 5 to 15 μm.

The sizes of the aerogel particles according to the invention may be measured by static light scattering using a commercial particle size analyzer such as the MasterSizer 2000 machine from Malvern. The data are processed on the basis of the Mie scattering theory. This theory, which is exact for isotropic particles, makes it possible to determine, in the case of non-spherical particles, an "effective" particle diameter. This theory is in particular described in the publication by Van de Hulst, H. C., "Light Scattering by Small Particles", Chapters 9 and 10, Wiley, New York, 1957.

According to one advantageous embodiment, the hydrophobic aerogel particles used in the present invention have a specific surface area per unit of mass (SM) ranging from 600 to 800 $m^2/g$ and a size, expressed as the volume mean diameter (D[0.5]), ranging from 5 to 20 μm and better still from 5 to 15 μm.

According to one preferred embodiment, use will be made more particularly of VM-2270, the particles of which have a mean size ranging from 5 to 15 microns and a specific surface area per unit of mass ranging from 600 to 800 $m^2/g$.

The hydrophobic aerogel particles used in the present invention may advantageously have a tapped density ρ ranging from 0.04 $g/cm^3$ to 0.10 $g/cm^3$ and preferably from 0.05 $g/cm^3$ to 0.08 $g/cm^3$.

In the context of the present invention, this density may be assessed according to the following protocol, known as the tapped density protocol: 40 g of powder are poured into a measuring cylinder and the cylinder is then placed on a Stay 2003 machine from Stampf Volumeter. The cylinder is then subjected to a series of 2500 tapping actions (this operation is repeated until the difference in volume between two consecutive tests is less than 2%); the final volume Vf of tapped powder is then measured directly on the cylinder. The tapped density is determined by the ratio: mass (m)/Vf, in this instance 40/Vf (Vf being expressed in $cm^3$ and m in g).

According to one embodiment, the hydrophobic aerogel particles used in the present invention have a specific surface area per unit of volume SV ranging from 5 to 60 $m^2/cm^3$, preferably from 10 to 50 $m^2/cm^3$ and better still from 15 to 40 $m^2/cm^3$.

The specific surface area per unit of volume is given by the relationship: SV=SM×ρ where ρ is the tapped density expressed in $g/cm^3$ and SM is the specific surface area per unit of mass expressed in $m^2/g$, as defined above.

According to one preferred embodiment, the hydrophobic aerogel particles according to the invention have a specific surface area per unit of mass (SM) ranging from 500 to 1500 $m^2/g$, preferably from 600 to 1200 $m^2/g$ and better still from 600 to 800 $m^2/g$, and have a size, expressed as the mean diameter (D[0.5]), ranging from 1 to 30 μm and/or an oil absorption capacity, measured at the wet point, ranging from 5 to 18 ml/g of particles, preferably from 6 to 15 ml/g and better still from 8 to 12 ml/g.

As hydrophobic silica aerogels that may be used in the invention, examples that may be mentioned include the aerogel sold under the name VM-2260 (INCI name: Silica silylate), by the company Dow Corning, the particles of which have a mean size of about 1000 microns and a specific surface area per unit of mass ranging from 600 to 800 $m^2/g$.

Mention may also be made of the aerogels sold by the company Cabot under the references Aerogel TLD 201, Aerogel OGD 201 and Aerogel TLD 203, Enova Aerogel MT 1100 and Enova Aerogel MT 1200.

Use will be made more particularly of the aerogel sold under the name VM-2270 (INCI name: Silica silylate), by the company Dow Corning, the particles of which have an average size ranging from 5 to 15 microns and a specific surface area per unit of mass ranging from 600 to 800 $m^2/g$.

The inorganic particles according to the invention may also be clay particles. Clays are products that are already well known per se, which are described, for example, in the publication Mineralogie des argiles [Mineralogy of Clays], S. Caillère, S. Hénin, M. Rautureau, 2nd Edition 1982, Masson.

Clays are silicates containing a cation that may be chosen from calcium, magnesium, aluminum, sodium, potassium and lithium cations, and mixtures thereof.

Mention may in particular be made of clays of the smectite family such as montmorillonites, hectorites, bentonites, beidellites and saponites, and also of the vermiculite, stevensite or chlorite family.

The clays may be of natural or synthetic origin. Preferably, clays that are cosmetically compatible and acceptable with keratin fibers such as the hair are used.

The clay may be chosen from montmorillonite, bentonite, hectorite, attapulgite and sepiolite, and mixtures thereof. Preferably, the clay is a bentonite or a hectorite. The clays may be chosen from organophilic clays. Organophilic clays are clays modified with a chemical compound chosen from quaternary amines, tertiary amines, amine acetates, imidazolines, amine soaps, fatty sulfates, alkyl aryl sulfonates and amine oxides, and mixtures thereof. Preferably, the organophilic clays according to the invention are clays modified with a chemical compound chosen from quaternary amines. Organophilic clays that may be mentioned include quaternium-18 bentonites such as those sold under the names Bentone 3, Bentone 38 and Bentone 38V by the company Elementis, Tixogel VP by the company United Catalyst, and Claytone 34, Claytone 40 and Claytone XL by the company Southern Clay; stearalkonium bentonites such as those sold under the names Bentone 27V by the company Elementis, Tixogel LG by the company United Catalyst, and Claytone AF and Claytone APA by the company Southern Clay; quaternium-18/benzalkonium bentonites such as those sold under the names Claytone HT and Claytone PS by the company Southern Clay. The organophilic clay is in particular chosen from modified hectorites such as hectorite modified with a $C_{10}$-$C_{12}$ fatty acid ammonium chloride, in particular distearyldimethylammonium chloride and stearylbenzyldimethylammonium chloride.

Preferably, the particles of one or more inorganic compounds are chosen from calcium carbonate, silica and, in particular, silica aerogels.

The solid particles, which are in particular water-insoluble, can also be chosen from organic or inorganic colored pigments, or else uncolored pearlescent agents. The colored organic pigments may be chosen from carmine lake, aniline black, azo yellow, quinacridone, phthalocyanine blue, the blue pigments codified in the Color Index under the references CI 42090, 69800, 69825, 73000, 74100 and 74160, the yellow pigments codified in the Color Index under the references CI 11680, 11710, 15985, 19140, 20040, 21100, 21108, 47000 and 47005, the green pigments codified in the Color Index under the references CI 61565, 61570 and 74260, the orange pigments codified in the Color Index under the references CI 11725, 15510, 45370 and 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915 and 75470, and the pigments obtained by oxidative polymerization of indole or phenolic derivatives as described in patent FR 2 679 771.

Mention may also be made of pigment pastes of organic pigment, such as the products sold by Hoechst under the names:

Cosmenyl Yellow 10G: Pigment Yellow 3 (CI 11710);
Cosmenyl Yellow G: Pigment Yellow 1 (CI 11680);
Cosmenyl Orange GR: Pigment Orange 43 (CI 71105);
Cosmenyl Red R: Pigment Red 4 (CI 12085);
Cosmenyl Carmine FB: Pigment Red 5 (CI 12490);
Cosmenyl Violet RL: Pigment Violet 23 (CI 51319);
Cosmenyl Blue A2R: Pigment Blue 15.1 (CI 74160);
Cosmenyl Green GG: Pigment Green 7 (CI 74260);
Cosmenyl Black R: Pigment Black 7 (CI 77266).

Mention may also be made, as pigments, of pearlescent pigments, such as colored pearlescent pigments, such as mica covered with titanium oxide and with iron oxides, mica covered with iron oxide, mica covered with titanium oxide and in particular with ferric blue or chromium oxide or mica covered with titanium oxide and with an organic pigment as defined above, and pearlescent pigments based on bismuth oxychloride. As pearlescent pigments, mention may be made of the pigments Cellini sold by Engelhard (Mica-TiO$_2$-lake), Prestige sold by Eckart (Mica-TiO$_2$), Prestige Bronze sold by Eckart (Mica-Fe$_2$O$_3$), Colorona sold by Merck (Mica-TiO$_2$—Fe2O$_3$); the gold-colored nacres in particular sold by the company Engelhard under the name Brilliant gold 212G (Timica), Gold 222C (Cloisonne), Sparkle gold (Timica), Gold 4504 (Chromalite) and Monarch gold 233X (Cloisonne); the bronze nacres sold in particular by the company Merck under the name Bronze fine (17384) (Colorona) and Bronze (17353) (Colorona) and by the company Engelhard under the name Super bronze (Cloisonne); the orange nacres sold in particular by the company Engelhard under the name Orange 363C (Cloisonne) and Orange MCR 101 (Cosmica) and by the company Merck under the name Passion orange (Colorona) and Matte orange (17449) (Microna); the brown nacres sold in particular by the company Engelhard under the name Nu-antique copper 340XB (Cloisonne) and Brown CL4509 (Chromalite); the nacres with a copper tint sold in particular by the company Engelhard under the name Copper 340A (Timica); the nacres with a red tint sold in particular by the company Merck under the name Sienna fine (17386) (Colorona); the nacres with a yellow tint sold in particular by the company Engelhard under the name Yellow (4502) (Chromalite); the red nacres with a gold tint sold in particular by the company Engelhard under the name Sunstone G012 (Gemtone); the pink nacres sold in particular by the company Engelhard under the name Tan opale 0005 (Gemtone); the black nacres with a gold tint sold in particular by the company Engelhard under the name Nu antique bronze 240 AB (Timica), the blue nacres sold in particular by the company Merck under the name Matte blue (17433) (Microna), the white nacres with a silvery tint sold in particular by the company Merck under the name Xirona Silver, and the golden-green pink-orange nacres sold in particular by the company Merck under the name Indian summer (Xirona), and mixtures thereof.

Among the pearlescent agents, mention may be made more particularly of:

esters of polyols having at least two carbon atoms and of long-chain fatty acids, which are preferentially $C_{10}$-$C_{30}$ and even more preferentially $C_{16}$-$C_{22}$; such as mono esters or diesters of polyols and of fatty acids; preferably, the polyols are ethylene glycol and polyalkylene glycols having from 2 to 10 ethylene oxide units;

ethers of long-chain fatty alcohols which are solid at a temperature less than or equal to approximately 30° C., such as, for example, the dialkyl ethers of formula: R—O—R', in which R and R', which may be identical or different, denote a linear or branched, saturated or unsaturated alkyl radical comprising from 10 to 30 carbon atoms and preferably from 14 to 24 carbon atoms, R and R' being chosen such that the compound is solid at a temperature less than or equal to approximately 30° C.

More particularly, R and R' denote a stearyl radical. A distearyl ether that can be used in the context of the present invention is sold under the name Cutina STE by the company HENKEL;

cyclodextrins and in particular β-cyclodextrin.

The pearlescent agents are preferentially chosen from ethylene glycol mono- or distearates (or glycol distearate), distearyl ether, 1-(hexadecyloxy)-2-octadecanol, β-cyclodextrin, and mixtures thereof.

Preferentially, the composition according to the invention comprises solid particles chosen from silicas, clays, pigments, pearlescent agents, pyridinethione salts and selenium disulfide, and quite particularly from silicas, pearlescent agents such as ethylene glycol mono- or distearate, distearyl ether, 1-(hexadecyloxy)-2-octadecanol, β-cyclodextrin, the zinc salt of pyridinethione, and selenium disulfide, and mixtures thereof.

The solid particles are preferably present in the composition in an amount ranging from 0.001% to 15% by weight, preferentially from 0.1% to 10% by weight and better still from 0.5% to 8% by weight, relative to the total weight of the composition.

Conditioning Agents

The composition according to the invention may also comprise at least one conditioning agent which may be chosen from non-polymer conditioning agents, polymer conditioning agents and mixtures thereof. The composition may quite obviously comprise several non-polymer or polymer conditioning agents.

In the context of the present application, the term "conditioning agent" is intended to mean any agent of which the function is to improve the cosmetic properties of the hair, in particular the softness, the sheen, the disentangling, the feel, the smoothness, the static electricity.

The non-polymer conditioning agents which can be used in the context of the present invention are preferably chosen from cationic surfactants, fatty esters other than triglycerides, fatty alcohols, vegetable oils, $C_6$-$C_{16}$ liquid hydrocarbons, hydrocarbons having more than 16 carbon atoms, ceramides, vegetable or animal waxes, and mixtures thereof.

1/ The cationic surfactant(s) which can be used according to the invention may for example be salts of optionally polyoxyalkylenated primary, secondary or tertiary fatty amines, quaternary ammonium salts, and mixtures thereof.

As quaternary ammonium salts, mention may particularly be made of:

those corresponding to the general formula (I) below:

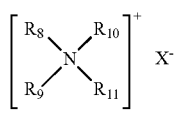

in which the groups $R_8$ to $R_{11}$, which may be identical or different, represent a linear or branched aliphatic group comprising from 1 to 30 carbon atoms or an aromatic group, such as aryl or alkylaryl, at least one of the groups $R_8$ to $R_{11}$ comprising from 8 to 30 carbon atoms and preferably from 12 to 24 carbon atoms. The aliphatic groups can comprise heteroatoms, such as, in particular, oxygen, nitrogen, sulfur and halogens. The aliphatic groups are chosen, for example, from $C_1$-$C_{30}$ alkyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate, and $C_1$-$C_{30}$ hydroxyalkyl groups, X⁻ is an anion chosen from the group of halides, phosphates, acetates, lactates, ($C_1$-$C_4$)alkyl sulfates, and ($C_1$-$C_4$)alkyl- or ($C_1$-$C_4$)alkylarylsulfonates.

Preference is given, among the quaternary ammonium salts of formula (I), on the one hand, to tetraalkylammonium chlorides, for instance dialkyldimethylammonium or alkyltrimethylammonium chlorides, in which the alkyl group comprises approximately from 12 to 22 carbon atoms, in particular behenyltrimethylammonium, distearyldimethylammonium, cetyltrimethylammonium or benzyldimethylstearylammonium chlorides, or, on the other hand, palmitylamidopropyltrimethylammonium chloride or stearamidopropyldimethyl(myristyl acetate)ammonium chloride, in particular sold under the name Ceraphyl® 70 by the company Van Dyk;

quaternary ammonium salts of imidazoline, for instance those of formula (II) below:

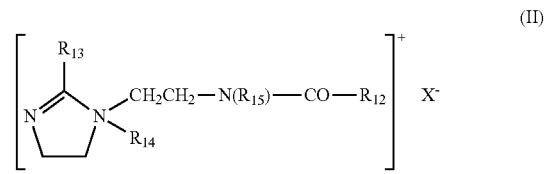

in which $R_{12}$ represents an alkenyl or alkyl group containing from 8 to 30 carbon atoms, for example tallow fatty acid derivatives, $R_{13}$ represents a hydrogen atom, a $C_1$-$C_4$ alkyl group or an alkenyl or alkyl group containing from 8 to 30 carbon atoms, $R_{14}$ represents a $C_1$-$C_4$ alkyl group, $R_{15}$ represents a hydrogen atom or a $C_1$-$C_4$ alkyl group, and X⁻ is an anion chosen from the group of halides, phosphates, acetates, lactates, ($C_1$-$C_4$)alkyl sulfates, and ($C_1$-$C_4$)alkyl- or ($C_1$-$C_4$)alkylarylsulfonates.

Preferably, $R_{12}$ and $R_{13}$ denote a mixture of alkenyl or alkyl groups comprising from 12 to 21 carbon atoms, for example derived from tallow fatty acids, $R_{14}$ denotes a methyl group and $R_{15}$ denotes a hydrogen atom. Such a product is sold, for example, under the name Rewoquat® W 75 by the company Rewo;

quaternary diammonium or triammonium salts, in particular of formula (III) below:

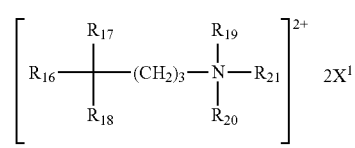

in which $R_{16}$ denotes an alkyl group containing approximately from 16 to 30 carbon atoms, which is optionally hydroxylated and/or interrupted with one or more oxygen atoms; $R_{17}$ is chosen from hydrogen, an alkyl group containing from 1 to 4 carbon atoms or a group —$(CH_2)_3$—$N^+$($R_{16a}$)($R_{17a}$)($R_{18a}$); $R_{16a}$, $R_{17a}$, $R_{18a}$, $R_{18}$, $R_{19}$, $R_{20}$ and $R_{21}$, which may be identical or different, are chosen from hydrogen or an alkyl group containing from 1 to 4 carbon atoms, and X⁻ is an anion chosen from the group of halides, acetates, phosphates, nitrates, ($C_1$-$C_4$)alkyl sulfates, and ($C_1$-$C_4$)alkyl- or ($C_1$-$C_4$)alkylarylsulfonates, in particular methyl sulfate and ethyl sulfate. Such compounds are, for example, Finquat CT-P, sold by the company Finetex (Quaternium 89), and Finquat CT, sold by the company Finetex (Quaternium 75), quaternary ammonium salts comprising one or more ester functions, for instance those of formula (IV) below:

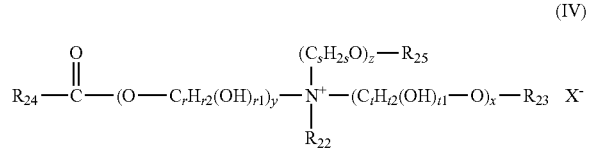

(IV)

in which:
$R_{22}$ is chosen from $C_1$-$C_6$ alkyl groups and $C_1$-$C_6$ hydroxyalkyl or dihydroxyalkyl groups,
$R_{23}$ is chosen from the group $R_{26}$—C(=O)—; linear or branched, saturated or unsaturated $C_1$-$C_{22}$ hydrocarbon-based groups $R_{27}$; and a hydrogen atom,
$R_{25}$ is chosen from the group $R_{28}$—C(=O)—; linear or branched, saturated or unsaturated $C_1$-$C_6$ hydrocarbon-based groups $R_{29}$; and a hydrogen atom,
$R_{24}$, $R_{26}$ and $R_{28}$, which may be identical or different, are chosen from linear or branched, saturated or unsaturated $C_7$-$C_{21}$ hydrocarbon-based groups,
r, s and t, which are identical or different, are integers having values from 2 to 6,
r1 and t1, which are identical or different, have the values 0 or 1,
r2+r1=2r and t1+t2=2 t,
y is an integer ranging from 1 to 10,
x and z, which may be identical or different, are integers ranging from 0 to 10,
$X^-$ is a simple or complex, organic or inorganic anion,
with the proviso that the sum x+y+z is from 1 to 15, that when x is 0 then $R_{23}$ denotes $R_{27}$, and that when z is 0 then $R_{25}$ denotes $R_{29}$.

The alkyl groups $R_{22}$ may be linear or branched, and more particularly linear.

Preferably, $R_{22}$ denotes a methyl, ethyl, hydroxyethyl or dihydroxypropyl group and more particularly a methyl or ethyl group.

Advantageously, the sum x+y+z is from 1 to 10.

When $R_{23}$ is an $R_{27}$ hydrocarbon group, it can be long and have from 12 to 22 carbon atoms or be short and have from 1 to 3 carbon atoms.

When $R_{25}$ is an $R_{29}$ hydrocarbon group, it preferably has from 1 to 3 carbon atoms. Advantageously, $R_{24}$, $R_{26}$ and $R_{28}$, which are identical or different, are chosen from saturated or unsaturated and linear or branched $C_{11}$-$C_{21}$ hydrocarbon groups and more particularly from saturated or unsaturated and linear or branched $C_{11}$-$C_{21}$ alkyl and alkenyl groups.

Preferably, x and z, which may be identical or different, are equal to 0 or 1.

Advantageously, y is equal to 1. Preferably, r, s and t, which may be identical or different, are equal to 2 or 3, and even more particularly are equal to 2. The anion $X^-$ is preferably a halide, preferably chloride, bromide or iodide, a $(C_1-C_4)$alkyl sulfate, or a $(C_1-C_4)$alkyl- or $(C_1-C_4)$alkylarylsulfonate. However, it is possible to use methanesulfonate, phosphate, nitrate, tosylate, an anion derived from an organic acid, such as acetate or lactate, or any other anion that is compatible with the ammonium containing an ester function.

The anion $X^-$ is more particularly still chloride, methyl sulfate or ethyl sulfate.

Use is made more particularly, in the composition according to the invention, of the ammonium salts of formula (IV) in which:
$R_{22}$ denotes a methyl or ethyl group,
x and y are equal to 1,
z is equal to 0 or 1,
r, s and t are equal to 2,
$R_{23}$ is chosen from the group $R_{26}$—C(=O)—, methyl, ethyl or $C_{14}$-$C_{22}$ hydrocarbon-based groups; and a hydrogen atom,
$R_{25}$ is chosen from the group $R_{28}$—C(=O)—; and a hydrogen atom,
$R_{24}$, $R_{26}$ and $R_{28}$, which may be identical or different, are chosen from linear or branched, saturated or unsaturated $C_{13}$-$C_{17}$ hydrocarbon-based groups, and preferably from linear or branched, saturated or unsaturated $C_{13}$-$C_{17}$ alkyl and alkenyl groups.

Advantageously, the hydrocarbon groups are linear.

Among the compounds of formula (IV), examples that may be mentioned include salts, in particular the chloride or methyl sulfate, of diacyloxyethyldimethylammonium, diacyloxyethylhydroxyethylmethylammonium, monoacyloxyethyldihydroxyethylmethylammonium, triacyloxyethylmethylammonium or monoacyloxyethylhydroxyethyldimethylammonium, and mixtures thereof. The acyl groups preferably contain 14 to 18 carbon atoms and are obtained more particularly from a vegetable oil, such as palm oil or sunflower oil. When the compound comprises several acyl groups, the latter can be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification is followed by a quaternization by means of an alkylating agent such as an alkyl halide, preferably methyl or ethyl halide, a dialkyl sulfate, preferably methyl or ethyl sulfate, methyl methanesulfonate, methyl para-toluenesulfonate, glycol chlorohydrin or glycerol chlorohydrin. Such compounds are, for example, sold under the names Dehyquart® by the company Henkel, Stepanquat® by the company Stepan, Noxamium® by the company Ceca or Rewoquat® WE 18 by the company Rewo-Witco.

The composition according to the invention can comprise, for example, a mixture of quaternary ammonium mono-, di- and triester salts with a predominance by weight of diester salts. Use may also be made of the ammonium salts comprising at least one ester functional group described in U.S. Pat. Nos. 4,874,554 and 4,137,180. Use may also be made of behenoylhydroxypropyltrimethylammonium chloride, for example, sold by the company KAO under the name Quartamin BTC 131.

Preferably, the ammonium salts containing at least one ester function comprise two ester functions.

The cationic surfactants present in the composition according to the invention are preferably chosen from cetyltrimethylammonium, behenyltrimethylammonium and dipalmitoylethylhydroxyethylmethylammonium salts, and mixtures thereof, and more particularly from behenyltrimethylammonium chloride, cetyltrimethylammonium chloride, and dipalmitoylethylhydroxyethylammonium methosulfate, and mixtures thereof.

2/ The fatty esters other than triglycerides may be chosen from fatty esters that are solid at ambient temperature and at atmospheric pressure (25° C., 1 atm), in particular other than solid fatty ester pearlescent agents, and liquid fatty esters, and also mixtures thereof.

Preferably, the solid fatty esters are esters of saturated carboxylic acids comprising at least 10 carbon atoms and of saturated fatty monoalcohols comprising at least 10 carbon atoms. The saturated acids or monoalcohols may be linear or branched. The saturated carboxylic acids preferably comprise from 10 to 30 carbon atoms and more particularly from 12 to 24 carbon atoms. They may optionally be hydroxylated. The saturated fatty monoalcohols preferably comprise from 10 to 30 carbon atoms and more particularly from 12 to 24 carbon atoms. Preferably, the solid fatty esters are chosen from myristyl myristate, cetyl myristate, stearyl myristate, myristyl palmitate, cetyl palmitate, stearyl palmitate, myristyl stearate, cetyl stearate and stearyl stearate, and mixtures thereof.

The liquid fatty esters may be esters of monoalcohols or of polyols with monoacids or polyacids, at least one of the alcohols and/or acids comprising at least one chain of more than 7 carbon atoms. Preferably, the liquid fatty ester according to the invention is chosen from esters of a fatty acid and of a monoalcohol. Preferably, at least one of the alcohols and/or acids is branched. Mention may be made of isopropyl myristate, isopropyl palmitate, isopropyl isononanoate, 2-ethylhexyl palmitate, 2-hexyldecyl laurate, 2-octyldecyl palmitate and 2-octyldodecyl myristate, and mixtures thereof.

Preferably, the fatty acids are liquid (at 25° C., 1 atm).

3/ The alcohol esters may be chosen from fatty alcohols that are solid at ambient temperature and at atmospheric pressure (25° C., 1 atm) and fatty alcohols that are liquid (at 25° C., 1 atm), and also mixtures thereof.

The term "fatty alcohol" is intended to mean a long-chain aliphatic alcohol comprising from 8 to 40 carbon atoms and comprising at least one hydroxyl group OH. These fatty alcohols are neither oxyalkylenated nor glycerolated. Preferably, the solid fatty alcohols have the structure R—OH with R denoting a linear alkyl group, optionally substituted with one or more hydroxyl groups, comprising from 8 to 40, better still from 10 to 30, or even from 12 to 24 and even better still from 14 to 22 carbon atoms.

The solid fatty alcohols that can be used may be chosen from, alone or as a mixture:
lauryl alcohol (1-dodecanol);
myristyl alcohol (1-tetradecanol);
cetyl alcohol (1-hexadecanol);
stearyl alcohol (1-octadecanol);
arachidyl alcohol (1-eicosanol);
behenyl alcohol (1-docosanol);
lignoceryl alcohol (1-tetracosanol);
ceryl alcohol (1-hexacosanol);
montanyl alcohol (1-octacosanol);
myricyl alcohol (1-triacontanol).

Preferentially, the solid fatty alcohol is chosen from cetyl alcohol, stearyl alcohol, behenyl alcohol and mixtures thereof such as cetylstearyl alcohol or cetearyl alcohol.

The solid fatty alcohols may be mixed, which means that several species, in particular of different chain lengths, may coexist in a commercial product, in the form of a mixture.

The liquid fatty alcohols, in particular the $C_{10}$-$C_{34}$ alcohols, preferably have branched carbon-based chains or contain one or more, preferably 1 to 3, unsaturations. They are preferably branched and/or unsaturated, and comprise from 12 to 40 carbon atoms, and are non-oxyalkylenated and non-oxyglycerolated. They preferably have the structure R—OH, in which R preferably denotes a branched $C_{12}$-$C_{24}$ alkyl or $C_{12}$-$C_{24}$ alkenyl group, R possibly being substituted with one or more hydroxyl groups. Preferably, the liquid fatty alcohol of the invention is a branched saturated alcohol. Preferably, R does not contain any hydroxyl groups. Mention may in particular be made of oleyl alcohol, linoleyl alcohol, linolenyl alcohol, isocetyl alcohol, isostearyl alcohol, 2-octyl-1-dodecanol, 2-butyloctanol, 2-hexyl-1-decanol, 2-decyl-1-tetradecanol and 2-tetradecyl-1-cetanol, and mixtures thereof.

Preferentially, the liquid fatty alcohol is 2-octyl-1-dodecanol.

Preferably, the fatty acids are liquid.

4/ The vegetable oils are preferably chosen from $C_8$-$C_{30}$ fatty acid triglycerides and preferentially from sweet almond oil, avocado oil, castor oil, olive oil, jojoba oil, sunflower oil, wheatgerm oil, sesame oil, groundnut oil, grapeseed oil, soybean oil, sesame oil, rapeseed oil, safflower oil, coconut oil, corn oil, hazelnut oil, shea butter oil, palm oil, apricot kernel oil, beauty-leaf oil, fish oils, and glyceryl tricaprocaprylate.

Mention may also be made of vegetable oils of formula $R_9COOR_{10}$ in which $R_9CO$ represents an acyl radical comprising from 8 to 30 carbon atoms and $R_{10}$ represents a linear or branched hydrocarbon-based chain containing from 3 to 30 carbon atoms, in particular alkyl or alkenyl, for example, purcellin oil or liquid jojoba wax.

5/ The $C_6$-$C_{16}$ liquid hydrocarbons may be linear or branched, and optionally cyclic, and are preferably alkanes. Examples that may be mentioned include hexane, cyclohexane, undecane, dodecane, isododecane, tridecane, perfluorohexane, and isoparaffins such as isohexadecane or isodecane.

The hydrocarbons having more than 16 carbon atoms may be linear or branched, and of inorganic or synthetic origin, and are preferably chosen from liquid paraffins, petroleum jelly, liquid petroleum jelly, polydecenes and hydrogenated polyisobutene such as Parleam®.

6/ According to the present invention, the term "ceramide" is intended to mean natural or synthetic ceramides and/or glycoceramides and/or pseudoceramides and/or neoceramides.

Ceramides are, for example, described in patent applications DE4424530, DE4424533, DE4402929, DE4420736, WO95/23807, WO94/07844, EP-A-0646572, WO95/16665, FR-2 673 179, EP-A-0227994, WO 94/07844, WO94/24097 and WO94/10131. Ceramides and/or glycoceramides of which the structure is described by Downing in the Journal of Lipid Research Vol. 35, 2060-2068, 1994, or those described in French patent application FR-2 673 179, are preferred.

The ceramides that can be used according to the present invention preferentially correspond to the general formula:

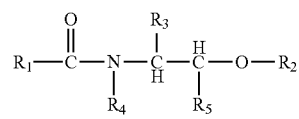

in which:
$R_1$ denotes:
either a linear or branched, saturated or unsaturated $C_1$-$C_{50}$, preferably $C_5$-$C_{50}$ hydrocarbon-based radical, it being possible for this radical to be substituted with one or more hydroxyl groups optionally esterified with an acid R7COOH, R7 being a linear or branched, saturated or unsaturated, optionally mono- or polyhydroxylated, $C_1$-$C_{35}$ hydrocarbon-based radical, it being possible for the hydroxyl(s) of the R7 radical to be esterified with a linear or branched, saturated or unsaturated, optionally mono- or polyhydroxylated, $C_1$-$C_{35}$ fatty acid;

or an R"—(NR—CO)—R' radical, where R denotes a hydrogen atom or a mono- or polyhydroxylated, preferentially monohydroxylated, $C_1$-$C_{20}$ hydrocarbon-based radical, and R' and R" are hydrocarbon-based radicals, the sum of the carbon atoms of which is between 9 and 30, R' being a divalent radical;

or an R8-O—CO—$(CH_2)_p$ radical, where R8 denotes a $C_1$-$C_{20}$ hydrocarbon-based radical, and p is an integer ranging from 1 to 12;

$R_2$ is chosen from a hydrogen atom, a radical of saccharide type, in particular a (glycosyl)n, (galactosyl)m or sulfogalactosyl radical, a sulfate or phosphate residue, a phosphorylethylamine radical and a phosphorylethylammonium radical, in which n is an integer ranging from 1 to 4 and m is an integer ranging from 1 to 8;

$R_3$ denotes a hydrogen atom or a saturated or unsaturated, hydroxylated or non-hydroxylated, $C_1$-$C_{33}$ hydrocarbon-based radical, it being possible for the hydroxyl(s) to be esterified with an inorganic acid or an acid R7COOH, R7 having the same meanings as above, it being possible for the hydroxyl(s) to be etherified with a (glycosyl)n, (galactosyl)m, sulfogalactosyl, phosphorylethylamine or phosphorylethylammonium radical, it being possible for $R_3$ to also be substituted with one or more $C_1$-$C_{14}$ alkyl radicals;

preferably, $R_3$ denotes a $C_{15}$-$C_{26}$ α-hydroxyalkyl radical, the hydroxyl group being optionally esterified with a $C_{16}$-$C_{30}$ α-hydroxy acid;

$R_4$ denotes a hydrogen atom, a methyl radical, an ethyl radical, a linear or branched, saturated or unsaturated, optionally hydroxylated, $C_3$-$C_{50}$ hydrocarbon-based radical, or a —$CH_2$—CHOH—$CH_2$—O—R6 radical in which R6 denotes a $C_{10}$-$C_{26}$ hydrocarbon-based radical or an R8-O—CO—$(CH_2)_p$ radical, in which R8 denotes a $C_1$-$C_{20}$ hydrocarbon-based radical and p is an integer ranging from 1 to 12;

$R_5$ denotes a hydrogen atom or a linear or branched, saturated or unsaturated, optionally mono- or polyhydroxylated, $C_1$-$C_{30}$ hydrocarbon-based radical, it being possible for the hydroxyl(s) to be etherified with a (glycosyl)n, (galactosyl)m, sulfogalactosyl, phosphorylethylamine or phosphorylethylammonium radical, with the proviso that, when $R_3$=$R_5$=H, or when $R_3$=H and $R_5$=methyl, then $R_4$ does not denote a hydrogen atom, a methyl radical or an ethyl radical.

The ceramides more particularly preferred are the compounds having the formula above for which $R_1$ denotes a saturated or unsaturated, optionally hydroxylated, alkyl derived from $C_{14}$-$C_{22}$ fatty acids; $R_2$ denotes a hydrogen atom; and $R_3$ denotes a linear, optionally hydroxylated, $C_{11}$-$C_{17}$, preferably $C_{13}$-$C_{17}$, radical. Even more preferentially, $R_3$ denotes an alpha-hydroxycetyl radical and $R_2$=$R_4$=$R_5$=H.

Mention may in particular be made, for example, of:
2-N-linoleoylaminooctadecane-1,3-diol,
2-N-oleoylaminooctadecane-1,3-diol (N-oleoyldihydrosphingosine),
2-N-palmitoylaminooctadecane-1,3-diol,
2-N-stearoylaminooctadecane-1,3-diol,
2-N-behenoylaminooctadecane-1,3-diol,
2-N-[2-hydroxypalmitoyl]aminooctadecane-1,3-diol,
2-N-stearoylaminooctadecane-1,3,4-triol and in particular N-stearoylphytosphingosine,
2-N-palmitoylaminohexadecane-1,3-diol,
or mixtures of these compounds.

Mention may also be made of specific mixtures, for instance mixtures of ceramide(s) 2 and of ceramide(s) 5 according to the Downing classification.

Mention may also be made of the compounds having the formula above for which $R_1$ denotes a saturated or unsaturated alkyl radical derived from $C_{12}$-$C_{22}$ fatty acids; $R_2$ denotes a galactosyl or sulfogalactosyl radical and $R_3$ denotes a saturated or unsaturated $C_{12}$-$C_{22}$ hydrocarbon-based radical, preferably a —CH=CH—$(CH_2)_{12}$—$CH_3$ group.

By way of example, mention may be made of the product formed from a mixture of glycoceramides, sold under the trade name Glycocer by the company Waitaki International Biosciences.

Use may also be made of the ceramides described in patent applications EP-A-0227994, EP-A-0 647 617, EP-A-0 736 522 and WO 94/07844.

Such compounds are, for example, Questamide H (bis(N-hydroxyethyl-N-cetyl)malonamide) sold by the company Quest, and cetylic acid N-(2-hydroxyethyl)-N-(3-cetyloxy-2-hydroxypropyl)amide.

Use may also be made of N-docosanoyl-N-methyl-D-glucamine, such as that described in patent application WO 94/24097.

7/ The vegetable or animal waxes that may be used can be chosen in particular from carnauba wax, candelilla wax, olive tree wax, rice wax, hydrogenated jojoba wax or absolute waxes of flowers, such as essential wax of blackcurrant flower, in particular that sold by the company Bertin (France), beeswaxes, and modified beeswaxes (cera bellina).

The polymer conditioning agents that may be used in the context of the present invention are preferably chosen from non-silicone cationic polymers, non-silicone amphoteric polymers, silicones, and mixtures thereof.

1/ The term "cationic polymer" is intended to mean any polymer comprising cationic groups and/or groups that can be ionized to cationic groups. Preferably, the cationic polymer is hydrophilic or amphiphilic. The cationic polymers may be chosen from all those already known per se for improving the cosmetic properties of the hair, namely in particular those described in documents EP 337 354, FR 2 270 846, FR 2 383 660, FR 2 598 611, FR 2 470 596 and FR 2 519 863.

The preferred cationic polymers are chosen from those that contain units comprising primary, secondary, tertiary and/or quaternary amine groups that may either form part of the main polymer chain or may be borne by a side substituent directly connected thereto.

The cationic polymers that may be used preferably have a weight-average molar mass (Mw) of between 500 and $5 \times 10^6$ approximately and preferably between $10^3$ and $3 \times 10^6$ approximately.

Among the cationic polymers, mention may more particularly be made of polymers of the polyamine, polyaminoamide and polyquaternary ammonium type, such as those described in FR 2 505 348 and FR 2 542 997.

Mention may in particular be made of:
(1) Homopolymers or copolymers derived from acrylic or methacrylic esters or amides and comprising at least one of the units of the following formulae:

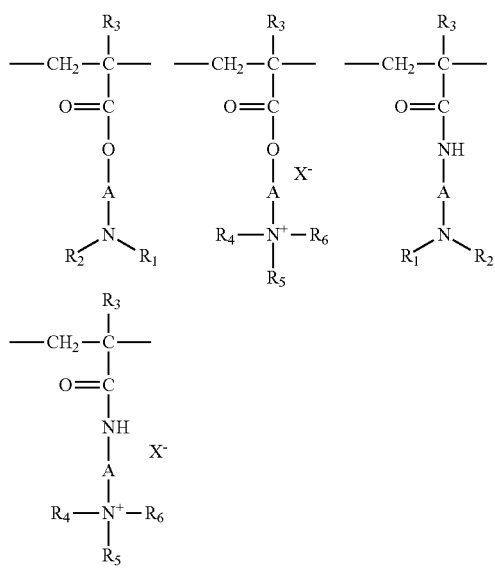

in which:
R₃, which may be identical or different, denote a hydrogen atom or a CH₃ radical;
A, which may be identical or different, represent a linear or branched divalent alkyl group of 1 to 6 carbon atoms, preferably 2 or 3 carbon atoms, or a hydroxyalkyl group of 1 to 4 carbon atoms;
R₄, R₅ and R₆, which may be identical or different, represent an alkyl group containing from 1 to 18 carbon atoms or a benzyl radical, preferably an alkyl group containing from 1 to 6 carbon atoms;
R₁ and R₂, which may be identical or different, represent a hydrogen atom or an alkyl group containing from 1 to 6 carbon atoms, preferably methyl or ethyl;
X denotes an anion derived from an inorganic or organic acid, such as a methosulfate anion or a halide such as chloride or bromide.

The copolymers of family (1) may also contain one or more units derived from comonomers that may be chosen from the family of acrylamides, methacrylamides, diacetone acrylamides, acrylamides and methacrylamides substituted on the nitrogen with lower (C₁-C₄)alkyls, acrylic or methacrylic acids or esters thereof, vinyllactams such as vinylpyrrolidone or vinylcaprolactam, and vinyl esters.

Among these copolymers of family (1), mention may be made of:
copolymers of acrylamide and of dimethylaminoethyl methacrylate quaternized with dimethyl sulfate or with a dimethyl halide, such as the product sold under the name Hercofloc by the company Hercules,
copolymers of acrylamide and of methacryloyloxyethyltrimethylammonium chloride, such as those described in EP 080 976 and those sold under the name Bina Quat P 100 by the company Ciba Geigy,
the copolymer of acrylamide and of methacryloyloxyethyltrimethylammonium methosulfate, such as the product sold under the name Reten by the company Hercules,
quaternized or non-quaternized vinylpyrrolidone/dialkylaminoalkyl acrylate or methacrylate copolymers, such as the products sold under the name Gafquat by the company ISP, for instance Gafquat 734 or Gafquat 755, or alternatively the products known as Copolymer 845, 958 and 937. These polymers are described in detail in French patents 2 077 143 and 2 393 573,
dimethylaminoethyl methacrylate/vinylcaprolactam/vinylpyrrolidone terpolymers, such as the product sold under the name Gaffix VC 713 by the company ISP,
vinylpyrrolidone/methacrylamidopropyldimethylamine copolymers, such as those sold under the name Styleze CC 10 by ISP;
quaternized vinylpyrrolidone/dimethylaminopropylmethacrylamide copolymers such as the product sold under the name Gafquat HS 100 by the company ISP,
preferably crosslinked polymers of methacryloyloxy(C₁-C₄)alkyltri(C₁-C₄)alkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homopolymerization or copolymerization being followed by crosslinking with an olefinically unsaturated compound, more particularly methylenebisacrylamide. A crosslinked acrylamide/methacryloyloxyethyltrimethylammonium chloride copolymer (20/80 by weight) in the form of a dispersion comprising 50% by weight of said copolymer in mineral oil may more particularly be used. This dispersion is sold under the name Salcare® SC 92 by the company Ciba. A crosslinked methacryloyloxyethyltrimethylammonium chloride homopolymer comprising about 50% by weight of the homopolymer in mineral oil or in a liquid ester can also be used. These dispersions are sold under the names Salcare® SC 95 and Salcare® SC 96 by the company Ciba.

(2) Cationic polysaccharides, in particular cationic celluloses and cationic galactomannan gums. Among the cationic polysaccharides, mention may be made more particularly of cellulose ether derivatives comprising quaternary ammonium groups, cationic cellulose copolymers or cellulose derivatives grafted with a water-soluble quaternary ammonium monomer and cationic galactomannan gums.

The cellulose ether derivatives comprising quaternary ammonium groups are in particular described in FR patent 1 492 597, and mention may be made of the polymers sold under the name Ucare Polymer JR (JR 400 LT, JR 125 and JR 30M) or LR (LR 400 and LR 30M) by the company Amerchol. These polymers are also defined in the CTFA dictionary as quaternary ammoniums of hydroxyethylcellulose that have reacted with an epoxide substituted with a trimethylammonium group.

Cationic cellulose copolymers or cellulose derivatives grafted with a water-soluble quaternary ammonium monomer are described in particular in U.S. Pat. No. 4,131,576, and mention may be made of hydroxyalkyl celluloses, for instance hydroxymethyl-, hydroxyethyl- or hydroxypropylcelluloses grafted, in particular, with a methacryloylethyltrimethylammonium, methacrylamidopropyltrimethylammonium or dimethyldiallylammonium salt. The commercial products corresponding to this definition are more particularly the products sold under the names Celquat L 200 and Celquat H 100 by the company National Starch.

The cationic galactomannan gums are described more particularly in U.S. Pat. Nos. 3,589,578 and 4,031,307, and mention may be made of guar gums comprising cationic trialkylammonium groups. Use is made, for example, of guar gums modified with a 2,3-epoxypropyltrimethylammonium salt (for example, a chloride). Such products are in particular sold under the names Jaguar C13 S, Jaguar C 15, Jaguar C 17 and Jaguar C162 by the company Rhodia.

(3) Polymers formed from piperazinyl units and divalent alkylene or hydroxyalkylene radicals containing linear or branched chains, optionally interrupted with oxygen, sulfur or nitrogen atoms or with aromatic or heterocyclic rings, and also the oxidation and/or quaternization products of these polymers. Such polymers are in particular described in FR 2 162 025 and FR 2 280 361.

(4) Water-soluble polyaminoamides prepared in particular by polycondensation of an acidic compound with a polyamine; these polyaminoamides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyaminoamide; these polyaminoamides can be alkylated or, if they comprise one or more tertiary amine functions, they can be quaternized. Such polymers are in particular described in French patents 2 252 840 and 2 368 508.

(5) Polyaminoamide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl radical comprises from 1 to 4 carbon atoms and preferably denotes methyl, ethyl or propyl. Such polymers are described in particular in FR 1 583 363. Among these derivatives, mention may be made more particularly of the adipic acid/dimethylaminohydroxypropyl/diethylenetriamine polymers sold under the name Cartaretine F, F4 or F8 by the company Sandoz.

(6) Polymers obtained by reacting a polyalkylene polyamine comprising two primary amine groups and at least one secondary amine group with a dicarboxylic acid chosen from diglycolic acid and saturated aliphatic dicarboxylic acids containing from 3 to 8 carbon atoms; the mole ratio between the polyalkylene polyamine and the dicarboxylic acid preferably being between 0.8:1 and 1.4:1; the resulting polyamino amide being reacted with epichlorohydrin in a mole ratio of epichlorohydrin relative to the secondary amine group of the polyamino amide preferably of between 0.5:1 and 1.8:1. Such polymers are in particular described in U.S. Pat. Nos. 3,227,615 and 2,961,347.

Polymers of this type are sold in particular under the name Hercosett 57 by the company Hercules Inc. or alternatively under the name PD 170 or Delsette 101 by the company Hercules in the case of the adipic acid/epoxypropyl/diethylenetriamine copolymer.

(7) Cyclopolymers of alkyldiallylamine or of dialkyldiallylammonium, such as the homopolymers or copolymers containing, as main constituent of the chain, units corresponding to formula (I) or (II):

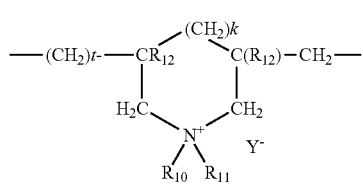
(I)

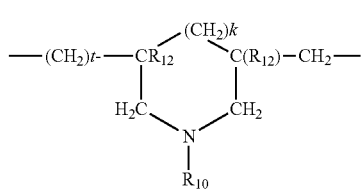
(II)

in which
k and t are equal to 0 or 1, the sum k+t being equal to 1;
$R_{12}$ denotes a hydrogen atom or a methyl radical;
$R_{10}$ and $R_{11}$, independently of each other, denote an alkyl group containing from 1 to 6 carbon atoms, a hydroxyalkyl group in which the alkyl group contains 1 to 5 carbon atoms, a $C_1$-$C_4$ amidoalkyl group; or alternatively $R_{10}$ and $R_{11}$ may denote, together with the nitrogen atom to which they are attached, heterocyclic groups such as piperidinyl or morpholinyl; $R_{10}$ and $R_{11}$, independently of each other, preferably denote an alkyl group containing from 1 to 4 carbon atoms;
$Y^-$ is an anion such as bromide, chloride, acetate, borate, citrate, tartrate, bisulfate, bisulfite, sulfate or phosphate.

These polymers are in particular described in FR 2 080 759 and FR 2 190 406. Mention may be made more particularly of the dimethyldiallylammonium salt (for example chloride) homopolymer for example sold under the name Merquat 100 by the company Nalco (and homologues thereof of low weight-average molar masses) and the copolymers of diallyldimethylammonium salts (for example chloride) and of acrylamide, sold in particular under the name Merquat 550 or Merquat 7SPR.

(8) Quaternary diammonium polymers comprising repeating units of formula:

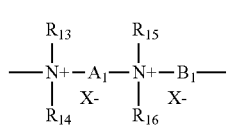
(III)

in which:
$R_{13}$, $R_{14}$, $R_{15}$ and $R_{16}$, which may be identical or different, represent aliphatic, alicyclic or arylaliphatic radicals comprising from 1 to 20 carbon atoms, or lower hydroxyalkylaliphatic radicals, or else $R_{13}$, $R_{14}$, $R_{15}$ and $R_{16}$, together or separately, constitute, with the nitrogen atoms to which they are attached, heterocycles optionally comprising a second non-nitrogen heteroatom, or else $R_{13}$, $R_{14}$, $R_{15}$ and $R_{16}$ represent a linear or branched $C_1$-$C_6$ alkyl radical substituted with a nitrile, ester, acyl, amide or —CO—O—$R_{17}$-D or —CO—NH—$R_{17}$-D group in which $R_{17}$ is an alkylene and D is a quaternary ammonium group;

A1 and B1 represent divalent polymethylene groups comprising from 2 to 20 carbon atoms, which may be linear or branched, saturated or unsaturated, and which may contain, linked to or intercalated in the main chain, one or more aromatic rings or one or more oxygen or sulfur atoms or sulfoxide, sulfone, disulfide, amino, alkylamino, hydroxyl, quaternary ammonium, ureido, amide or ester groups, and $X^-$ denotes an anion derived from an inorganic or organic acid;

it being understood that $A_1$, $R_{13}$ and $R_{15}$ can form, with the two nitrogen atoms to which they are attached, a piperazine ring;

in addition, if $A_1$ denotes a linear or branched, saturated or unsaturated alkylene or hydroxyalkylene radical, $B_1$ may also denote a group $-(CH_2)_n-CO-D-OC-(CH_2)_n-$ in which D denotes:

a) a glycol residue of formula $-O-Z-O-$, in which Z denotes a linear or branched hydrocarbon-based radical, or a group corresponding to one of the following formulae: $-(CH_2-CH_2-O)_x-CH_2-CH_2-$ and $-[CH_2-CH(CH_3)-O]_y-CH_2-CH(CH_3)-$, where x and y denote an integer from 1 to 4, representing a defined and unique degree of polymerization or any number from 1 to 4 representing an average degree of polymerization;

b) a bis-secondary diamine residue, such as a piperazine derivative;

c) a bis-primary diamine residue of formula: $-NH-Y-NH-$, where Y denotes a linear or branched hydrocarbon-based radical, or else the divalent radical $-CH_2-CH_2-S-S-CH_2-CH_2-$;

d) a ureylene group of formula: $-NH-CO-NH-$.

Preferably, $X^-$ is an anion such as chloride or bromide.

These polymers have a number-average molar mass (Mn) generally of between 1000 and 100 000.

Polymers of this type are described in particular in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

Mention may be made more particularly of polymers that are composed of repeating units corresponding to the formula:

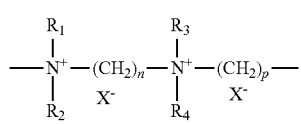 (IV)

in which $R_1$, $R_2$, $R_3$ and $R_4$, which may be identical or different, denote an alkyl or hydroxyalkyl radical containing from 1 to 4 carbon atoms approximately, n and p are integers ranging from 2 to 20 approximately, and $X^-$ is an anion derived from an inorganic or organic acid.

A particularly preferred compound of formula (IV) is that for which $R_1$, $R_2$, $R_3$ and $R_4$ represent a methyl radical and n=3, p=6 and X=Cl, known as Hexadimethrine chloride according to the INCI (CTFA) nomenclature.

(9) Polyquaternary ammonium polymers comprising units of formula (V):

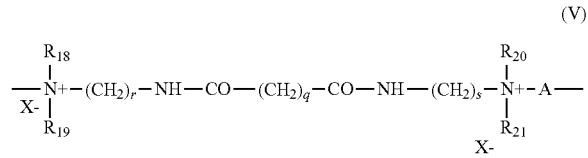 (V)

in which:

$R_{18}$, $R_{19}$, $R_{20}$ and $R_{21}$, which may be identical or different, represent a hydrogen atom or a methyl, ethyl, propyl, β-hydroxyethyl, β-hydroxypropyl or $CH_2CH_2(OCH_2CH_2)_pOH$ radical, in which p is equal to 0 or to an integer between 1 and 6, with the proviso that $R_{18}$, $R_{19}$, $R_{20}$ and $R_{21}$ do not simultaneously represent a hydrogen atom, r and s, which may be identical or different, are integers between 1 and 6, q is equal to 0 or to an integer between 1 and 34, $X^-$ denotes an anion such as a halide, A denotes a dihalide radical or preferably represents $-CH_2-CH_2-O-CH_2-CH_2-$.

Such compounds are described in particular in patent application EP-A-122 324. Examples that may be mentioned include the products Mirapol® A 15, Mirapol® AD1, Mirapol® AZ1 and Mirapol® 175 sold by the company Miranol.

(10) Quaternary polymers of vinylpyrrolidone and of vinylimidazole, for instance the products sold under the names Luviquat® FC 905, FC 550 and FC 370 by the company BASF.

(11) Polyamines such as Polyquart® H sold by Cognis, referred to under the name Polyethylene glycol (15) tallow polyamine in the CTFA dictionary.

(12) Polymers comprising in their structure:

(a) one or more units corresponding to formula (A) below:

 (A)

(b) optionally one or more units corresponding to formula (B) below:

 (B)

In other words, these polymers may be chosen in particular from homopolymers or copolymers comprising one or more units derived from vinylamine and optionally one or more units derived from vinylformamide.

Preferably, these cationic polymers are chosen from polymers comprising, in their structure, from 5 mol % to 100 mol % of units corresponding to formula (A) and from 0 to 95 mol % of units corresponding to formula (B), preferentially from 10 mol % to 100 mol % of units corresponding to formula (A) and from 0 to 90 mol % of units corresponding to formula (B).

These polymers may be obtained, for example, by partial hydrolysis of polyvinylformamide. This hydrolysis can be carried out in an acidic or basic medium.

The weight-average molecular weight of said polymer, measured by light scattering, may range from 1000 to 3 000 000 g/mol, preferably from 10 000 to 1 000 000 and more particularly from 100 000 to 500 000 g/mol.

The cationic charge density of these polymers may range from 2 meq/g to 20 meq/g, preferably from 2.5 to 15 meq/g and more particularly from 3.5 to 10 meq/g.

The polymers comprising units of formula (A) and optionally units of formula (B) are sold in particular under the name Lupamin by the company BASF, for instance, and in a non-limiting manner, the products sold under the names Lupamin 9095, Lupamin 5095, Lupamin 1095, Lupamin 9030 and Lupamin 9010.

Other cationic polymers that may be used in the context of the invention are cationic proteins or cationic protein hydrolysates, polyalkyleneimines, in particular polyethyleneimines, polymers comprising vinylpyridine or vinylpyridinium units, condensates of polyamines and of epichlorohydrin, quaternary polyureylenes and chitin derivatives.

Preferably, the non-silicone cationic polymers are chosen from those of families (1), (2), (7) and (10) mentioned above, and quite particularly from those of family (2).

Among the cationic polymers mentioned above, the ones that may preferably be used are cationic polysaccharides, in particular cationic celluloses and cationic galactomannan gums, and in particular quaternary cellulose ether derivatives such as the products sold under the name JR 400 by the company Amerchol, cationic cyclopolymers, in particular dimethyldiallylammonium salt (for example chloride) homopolymers or copolymers, sold under the names Merquat 100, Merquat 550 and Merquat S by the company Nalco, and homologs thereof of low weight-average molecular weights, quaternary polymers of vinylpyrrolidone and of vinylimidazole, optionally crosslinked homopolymers or copolymers of methacryloyloxy($C_1$-$C_4$)alkyltri($C_1$-$C_4$)alkylammonium salts, and mixtures thereof.

2/ The non-silicone amphoteric polymers may preferably be chosen from amphoteric polymers comprising the repetition of:

(i) one or more units derived from a monomer of (meth) acrylamide type, (ii) one or more units derived from a monomer of (meth) acrylamidoalkyltrialkylammonium type, and (iii) one or more units derived from an acidic monomer of (meth)acrylic acid type.

Preferably, the units derived from a monomer of (meth) acrylamide type (i) are units of structure (I) below:

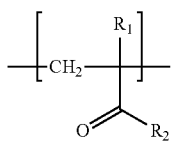
(I)

in which $R_1$ denotes H or $CH_3$ and $R_2$ is chosen from an amino, dimethylamino, tert-butylamino, dodecylamino or —NH—$CH_2$OH radical.

Preferably, said amphoteric polymer comprises the repetition of only one unit of formula (I).

The unit derived from a monomer of (meth)acrylamide type of formula (I) in which $R_1$ denotes H and $R_2$ is an amino radical ($NH_2$) is particularly preferred. It corresponds to the acrylamide monomer per se.

Preferably, the units derived from a monomer of (meth) acrylamidoalkyltrialkylammonium type (ii) are units of structure (II) below:

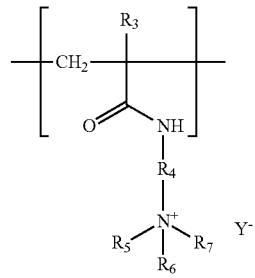
(II)

in which:
$R_3$ denotes H or $CH_3$,
$R_4$ denotes a $(CH_2)_k$ group with k an integer ranging from 1 to 6 and preferably from 2 to 4;
$R_5$, $R_6$, and $R_7$, which may be identical or different, each denote an alkyl group containing from 1 to 4 carbon atoms;
$Y^-$ is an anion such as bromide, chloride, acetate, borate, citrate, tartrate, bisulfate, bisulfite, sulfate or phosphate.

Preferably, said amphoteric polymer comprises the repetition of only one unit of formula (II).

Among these units derived from a monomer of (meth) acrylamidoalkyltrialkylammonium type of formula (II), the ones that are preferred are those derived from the methacrylamidopropyltrimethylammonium chloride monomer, for which $R_3$ denotes a methyl radical, k is equal to 3, $R_5$, $R_6$ and $R_7$ denote a methyl radical, and $Y^-$ denotes a chloride anion.

Preferably, the units derived from a monomer of (meth) acrylic acid type (iii) are units of formula (III):

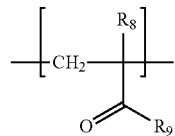
(III)

in which $R_8$ denotes H or $CH_3$ and $R_9$ denotes a hydroxyl radical or an —NH—C($CH_3$)$_2$—$CH_2$—$SO_3$H radical.

The preferred units of formula (III) correspond to the acrylic acid, methacrylic acid and 2-acrylamino-2-methylpropanesulfonic acid monomers.

Preferably, the unit derived from a monomer of (meth) acrylic acid type of formula (III) is that derived from acrylic acid, for which $R_8$ denotes a hydrogen atom and $R_9$ denotes a hydroxyl radical.

The acidic monomer(s) of (meth)acrylic acid type may be non-neutralized or partially or totally neutralized with an organic or inorganic base.

Preferably, said amphoteric polymer comprises the repetition of only one unit of formula (III).

According to a preferred embodiment of the invention, the amphoteric polymer(s) of this type comprise at least 30 mol % of units derived from a monomer of (meth)acrylamide type (i). Preferably, they comprise from 30 mol % to 70 mol % and more preferably from 40 mol % to 60 mol % of units derived from a monomer of (meth)acrylamide type.

The content of units derived from a monomer of (meth) acrylamidoalkyltrialkylammonium type (ii) may advantageously be from 10 mol % to 60 mol % and preferentially from 20 mol % to 55 mol %.

The content of units derived from an acidic monomer of (meth)acrylic acid type (iii) may advantageously be from 1 mol % to 20 mol % and preferentially from 5 mol % to 15 mol %.

According to a particularly preferred embodiment of the invention, the amphoteric polymer of this type comprises:
- from 30 mol % to 70 mol % and more preferably from 40 mol % to 60 mol % of units derived from a monomer of (meth)acrylamide type (i),
- from 10 mol % to 60 mol % and preferentially from 20 mol % to 55 mol % of units derived from a monomer of (meth)acrylamidoalkyltrialkylammonium type (ii), and
- from 1 mol % to 20 mol % and preferentially from 5 mol % to 15 mol % of units derived from a monomer of (meth)acrylic acid type (iii).

Amphoteric polymers of this type may also comprise additional units, other than the units derived from a monomer of (meth)acrylamide type, of (meth)acrylamidoalkyltrialkylammonium type and of (meth)acrylic acid type as described above.

However, according to a preferred embodiment of the invention, said amphoteric polymers consist solely of units derived from monomers of (meth)acrylamide type (i), of (meth)acrylamidoalkyltrialkylammonium type (ii) and of (meth)acrylic acid type (iii).

Mention may be made, as examples of amphoteric polymers which are particularly preferred, of acrylamide/methacrylamidopropyltrimethylammonium chloride/acrylic acid terpolymers. Such polymers are listed in the CTFA International Cosmetic Ingredient Dictionary, 10th edition 2004, under the name Polyquaternium 53. Corresponding products are in particular sold under the names Merquat 2003 and Merquat 2003 PR by the company Nalco.

As another type of amphoteric polymer that may be used, mention may also be made of copolymers based on (meth)acrylic acid and on a dialkyldiallylammonium salt, such as copolymers of (meth)acrylic acid and of dimethyldiallylammonium chloride. An example that may be mentioned is Merquat 280 sold by the company Nalco.

3/ The silicones that may be used can be chosen from polydialkylsiloxanes, in particular polydimethylsiloxanes (PDMSs), and organomodified polysiloxanes comprising at least one functional group preferably chosen from aryl groups, amino groups, alkoxy groups and polyoxyethylenated or polyoxypropylenated groups.

Silicones are in particular defined in greater detail in Walter Noll's *Chemistry and Technology of Silicones* (1968), Academic Press. They may be volatile or nonvolatile, and may be in the form of an oil, a gum or a resin; silicone oils and gums are preferred.

When they are volatile, the silicones may be more particularly chosen from those with a boiling point of between 60° C. and 260° C., and even more particularly from: (i) cyclic polydialkylsiloxanes comprising from 3 to 7 and preferably from 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, and Silbione® 70045 V5 by Rhodia, and mixtures thereof.

Mention may also be made of cyclocopolymers of the dimethylsiloxanes/methylalkylsiloxane type, such as Volatile Silicone® FZ 3109 sold by the company Union Carbide, of formula:

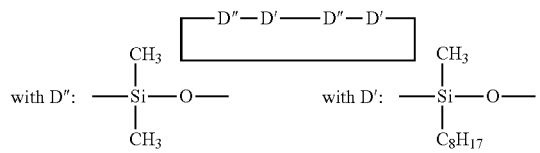

Mention may also be made of mixtures of cyclic polydialkylsiloxanes with organosilicon compounds, such as the mixture of octamethylcyclotetrasiloxane and tetra(trimethylsilyl)pentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5 \times 10^{-6}$ m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, January 76, P. 27-32—TODD & BYERS "Volatile silicone fluids for cosmetics".

Use is preferably made of nonvolatile polydialkylsiloxanes, polyorganosiloxanes modified with the organofunctional groups above, and mixtures thereof. These silicones are more particularly chosen from polydialkylsiloxanes, among which mention may be made mainly of polydimethylsiloxanes bearing trimethylsilyl end groups. The viscosity of the silicones is measured at 25° C. according to ASTM Standard 445 Appendix C.

Among these polydialkylsiloxanes, mention may be made of the following commercial products:
- the Silbione® oils of the 47 and 70 047 series or the Mirasil® oils sold by Rhodia, such as, for example, the oil 70 047 V 500 000;
- the oils of the Mirasil® series sold by the company Rhodia;
- the oils of the 200 series from the company Dow Corning, such as DC$_{200}$ with a viscosity of 60 000 mm$^2$/s;
- the Viscasil® oils from General Electric and certain oils of the SF series (SF 96, SF 18) from General Electric.

Mention may also be made of polydimethylsiloxanes bearing dimethylsilanol end groups known under the name dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are poly(C$_1$-C$_{20}$)dialkylsiloxanes.

Products that can be used more particularly in accordance with the invention are mixtures such as:
- the mixtures formed from a polydimethylsiloxane hydroxylated at the chain end, or dimethiconol (CTFA), and from a cyclic polydimethylsiloxane, also known as cyclomethicone (CTFA), such as the product Q2 1401 sold by the company Dow Corning.

The organomodified silicones that may be used in the present invention are in particular silicones as defined above and comprising in their structure one or more organofunctional groups attached via a hydrocarbon-based group.

The organomodified silicones may be polydiarylsiloxanes, in particular polydiphenylsiloxanes, and polyalkylarylsiloxanes functionalized with the organofunctional groups mentioned previously.

The polyalkylarylsiloxanes are particularly chosen from linear and/or branched polydimethyl/methylphenylsiloxanes and polydimethyl/diphenylsiloxanes with a viscosity ranging from $1 \times 10^{-5}$ to $5 \times 10^{-2}$ m$^2$/s at 25° C.

Among these polyalkylarylsiloxanes, examples that may be mentioned include the products sold under the following names:

the Silbione® oils of the 70 641 series from Rhodia;
the oils of the Rhodorsil® 70 633 and 763 series from Rhodia;
the oil Dow Corning 556 Cosmetic Grade Fluid from Dow Corning;
the silicones of the PK series from Bayer, such as the product PK20;
the silicones of the PN and PH series from Bayer, such as the products PN1000 and PH1000;
certain oils of the SF series from General Electric, such as SF 1023, SF 1154, SF 1250 and SF 1265.

Among the organomodified silicones, mention may also be made of polyorganosiloxanes comprising:

substituted or unsubstituted amine groups, for instance the products sold under the names GP 4 Silicone Fluid and GP 7100 by the company Genesee. The substituted amine groups are in particular $C_1$-$C_4$ alkyl groups;
alkoxy groups such as the product sold under the name Silicone Copolymer F-755 by SWS Silicones;
oxyethylenated or oxypropylenated groups.

In one variant of the invention, the silicones are not organomodified.

Preferably, the silicones are cationic or nonionic.

Preferentially, the composition according to the invention comprises one or more conditioning agents chosen from vegetable oils (triglycerides), fatty esters which are preferably liquid, cationic surfactants, the $C_6$-$C_{16}$ liquid hydrocarbons, hydrocarbons having more than 16 carbon atoms; silicones and non-silicone cationic polymers; and also mixtures thereof.

Even more preferentially, the composition according to the invention comprises one or more conditioning agents chosen from silicones and non-silicone cationic polymers, and also mixtures thereof.

The conditioning agents are preferably present in the composition according to the invention in an amount ranging from 0.001% to 20% by weight, preferentially from 0.1% to 10% by weight, even better still from 0.2% to 8% by weight, or even from 0.4% to 5% by weight, relative to the total weight of the composition.

Antidandruff Agents

The composition according to the invention may also comprise at least one non-particulate antidandruff agent; it may quite obviously comprise several antidandruff agents of this type.

The non-particulate antidandruff agents that may be used according to the invention are in particular chosen from the following families:

1) 1-hydroxy-2-pyrrolidone derivatives represented in particular by the formula:

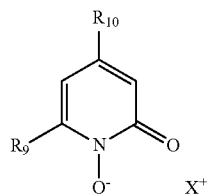

in which:

$R_9$ represents an alkyl group containing from 1 to 17 carbon atoms, an alkenyl group containing from 2 to 17 carbon atoms, a cycloalkyl group containing from 5 to 8 carbon atoms, a bicycloalkyl group containing from 7 to 9 carbon atoms; a cycloalkylalkyl group, an aryl group, an aralkyl group with an alkyl containing from 1 to 4 carbon atoms, an arylalkenyl group with an alkenyl containing from 2 to 4 carbon atoms, aryloxyalkyl or arylmercaptoalkyl with an alkyl containing from 1 to 4 carbon atoms, a furylalkenyl group with an alkenyl or a furyl containing from 2 to 4 carbon atoms, an alkoxy group containing from 1 to 4 carbon atoms, a nitro group, a cyano group or a halogen atom;

$R_{10}$ represents a hydrogen atom, a $C_1$-$C_4$ alkyl group, a $C_2$-$C_4$ alkenyl group, a halogen atom, a phenyl group or a benzyl group;

X represents an organic or inorganic base, an alkali metal or alkaline-earth metal ion or an ammonium ion.

Mention may in particular be made of 1-hydroxy-4-methyl-2-pyridone, 1-hydroxy-6-methyl-2-pyridone, 1-hydroxy-4,6-dimethyl-2-pyridone, 1-hydroxy-4-methyl-6-(2,4,4-trimethylpentyl)-2-pyridone, 1-hydroxy-4-methyl-6-cyclohexyl-2-pyridone, 1-hydroxy-4-methyl-6-(methylcyclohexyl)-2-pyridone, 1-hydroxy-4-methyl-6-(2-bicyclo[2,2,1]heptyl)-2-pyridone, 1-hydroxy-4-methyl-6-(4-methylphenyl)-2-pyridone, 1-hydroxy-4-methyl-6-[1-(4-nitrophenoxyl)butyl]-2-pyridone, 1-hydroxy-4-methyl-6-(4-cyanophenoxymethyl)-2-pyridone, 1-hydroxy-4-methyl-6-(phenylsulfonylmethyl)-2-pyridone and 1-hydroxy-4-methyl-6-(4-bromobenzyl)-2-pyridone.

These compounds may be used in the form of salts with organic or inorganic bases. Examples of organic bases are in particular alkanolamines of low molecular weight such as ethanolamine, diethanolamine, N-ethylethanolamine, triethanolamine, diethylaminoethanol and 2-amino-2-methylpropanediol; non-volatile bases such as ethylenediamine, hexamethylenediamine, cyclohexylamine, benzylamine and N-methylpiperazine; quaternary ammonium hydroxides, such as trimethylbenzyammonium hydroxide; guanidine and derivatives thereof, and particularly alkyl derivatives thereof. Examples of inorganic bases are in particular salts of alkali metals, e.g. sodium or potassium; ammonium salts, salts of an alkaline-earth metal, such as magnesium or calcium; salts of di-, tri- or tetravalent cationic metals, such as zinc, aluminum or zirconium.

Alkanolamines, ethylenediamine and inorganic bases such as alkali metal salts are preferred.

A compound that is particularly preferred is the one for which $R_9$ denotes the group:

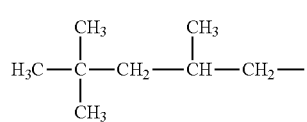

$R_{10}$ denotes a methyl group and $X^+$ denotes $N^+H_3CH_2CH_2OH$.

This compound is sold, for example, under the name Octopyrox (1-hydroxy-4-methyl-6-(2,4,4-trimethylpentyl)-2-pyridone, monoethanolamine salt) by the company Hoechst;

2) 2,2'-dithiobis(pyridine N-oxide) of formula:

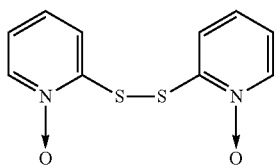 [SMILES: [O-][n+]1ccccc1SSc1cccc[n+]1[O-]]

These compounds may be introduced into the compositions in the form of inorganic salts. An example of an inorganic salt is magnesium sulfate;

3) trihalocarbamides, in particular having the formula:

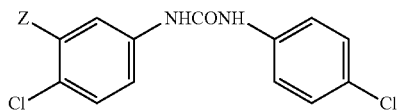

in which Z represents a halogen atom such as chlorine or a $C_1$-$C_4$ trihaloalkyl group such as $CF_3$;

4) triclosan, represented by the formula:

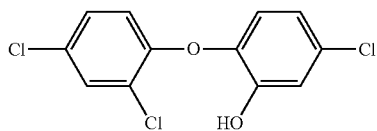 [SMILES: Oc1cc(Cl)ccc1Oc1ccc(Cl)cc1Cl]

5) azole compounds such as climbazole, ketoconazole, clotrimazole, econazole, isoconazole and miconazole, 6) antifungal polymers such as amphotericin B or nystatin;

7) extracts of one or more non-photosynthetic, non-fruiting filamentous bacteria.

The bacterial extracts that may be used according to the invention are in particular chosen from non-photosynthetic, non-fruiting filamentous bacteria as defined according to the classification in Bergey's *Manual of Systemic Bacteriology*, volume 3, section 23, 9th edition 1989.

Among the bacteria that may be used, mention will be made more particularly of bacteria belonging to the order Beggiatoales, and in particular bacteria belonging to the genus *Beggiotoa*, for instance various strains of *Beggiotoa alba*. According to the definition, *B. alba* corresponds to the former names *Beggiotoa arachnoidea*, *B. gigantea*, *B. leptomiformis*, *B. minima* and *B. mirabilis* of Bergey's manual, 8th edition. Mention may moreover be made of bacteria belonging to the genus *Vitreoscilla*, which is known to be close to and often difficult to distinguish from the genus *Beggiatoa*. The bacteria that have just been defined, and several of which have been described, generally have an aquatic habitat, and may be found in particular in spring water sources. Among the bacteria that can be used, mention may, for example, be made of *Vitreoscilla beggiatoïdes* (ATCC 43181) and *Beggiatoa alba* (ATCC$_{33555}$); preferentially, the use of the extract of *Vitreoscilla filiformis*, in particular the ATCC 15551 strain, metabolites thereof and fractions thereof.

Moreover, it is known that culturing non-photosynthetic, non-fruiting filamentous bacteria is relatively difficult, as is the production of pure cultures. Use will preferentially be made of the culture described in patent application WO 94/02158. The term "non-photosynthetic, non-fruiting filamentous bacteria" is intended to mean not only the culture supernatant but also the biomass obtained after culturing said bacteria, the envelopes or envelope fractions, or the extracts of the biomass obtained by treating this biomass.

To prepare the extract according to the invention, said bacteria can be cultured and then separated from the biomass obtained, for example by filtration, centrifugation, coagulation and/or lyophilization.

The extracts that may be used may in particular be prepared according to the process described in patent application WO-A-93/00741. Thus, after culturing, the bacteria are concentrated by centrifugation. The biomass obtained is autoclaved. This biomass may be lyophilized to constitute what is known as the lyophilized extract. Any lyophilization method known to those skilled in the art may be used to prepare this extract.

The supernatant fraction of this biomass may also be filtered in a sterile container to remove the particles in suspension.

The terms "envelopes" and "envelope fractions" refer herein to the bacterial wall and possibly the subjacent membranes;

8) ellagic acid, ethers thereof, salts of ellagic acid and salts of ethers thereof; and also ellagic acid tannins.

Ellagic acid, also known as 2,3,7,8-tetrahydroxy-1-benzopyrano[5,4,3-cde]-1-benzopyran-5,10-dione, is a well-known molecule which is present in the plant kingdom. Reference may be made to the Merck Index 20th edition (1996), No. 3588.

Ellagic acid has the following chemical formula:

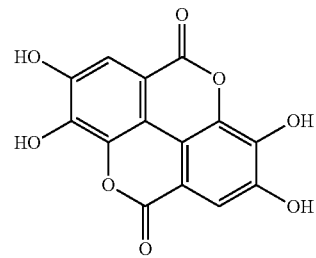 [SMILES: O=c1oc2c(O)c(O)cc3c(=O)oc4c(O)c(O)cc1c4c23]

which comprises four fused rings.

Document FR-A-1 478 523 discloses a process for purifying ellagic acid and also the purified ellagic acids obtained via such a process.

The ellagic acid ether(s) which can be used according to the invention is (are) preferably chosen from the mono-, di-, tri- or polyethers obtained by etherification of one or more hydroxyl groups (one of the four OH groups of ellagic acid) of ellagic acid to one or more groups OR, R being chosen from $C_2$-$C_{20}$ alkyl groups, polyoxyalkylene groups, and in particular polyoxyethylene and/or polyoxypropylene groups, and groups derived from one or more mono- or polysaccharides, such as, for example, the group having the formula below:

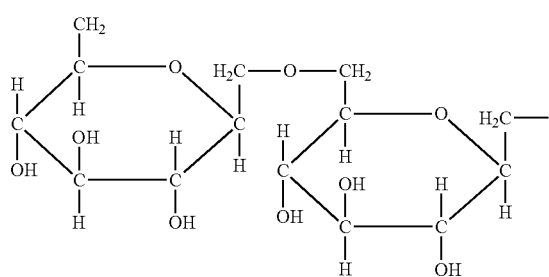

In the case of the ellagic acid di-, tri- or polyethers, the R groups as defined above may be identical or different.

Such ethers are described in patent U.S. Pat. No. 5,073,545. These ellagic acid ethers are preferably chosen from 3,4-di-O-methyl ellagic acid, 3,3',4-tri-O-methyl ellagic acid and 3,3'-di-O-methyl ellagic acid.

The salt(s) of ellagic acid and/or of ethers thereof which can be used according to the invention is (are) preferably chosen from the salts of alkali metals or alkaline-earth metals, such as sodium, potassium, calcium and magnesium, the ammonium salt and the amine salts such as triethanolamine, monoethanolamine, arginine and lysine salts. Preferably, the salt(s) of ellagic acid and/or of ethers thereof which can be used according to the invention is (are) chosen from alkali metal or alkaline-earth metal salts, in particular the sodium, potassium, calcium or magnesium salts;

9) other antidandruff agents are allantoin, coal or wood tars and derivatives thereof, in particular cade oil, undecylenic acid, fumaric acid, and allylamines such as terbinafine.

Preferentially, the composition according to the invention comprises one or more non-particulate antidandruff agents chosen from piroctone olamine, ellagic acid, and mixtures thereof.

The non-particulate antidandruff agents are preferably present in the composition in an amount ranging from 0.01% to 10% by weight, preferentially from 0.2% to 5% by weight and even better still from 0.5% to 3% by weight relative to the total weight of the composition.

Polyols

The composition according to the invention may also comprise at least one polyol; it may quite obviously comprise several polyols.

Preferably, the polyol(s) of the invention is (are) not polysaccharides.

The polyols that may be used in the context of the present invention preferably have the formula:

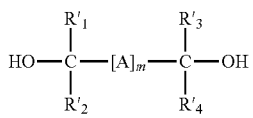

in which:
R'$_1$, R'$_2$, R'$_3$ and R'$_4$ denote, independently of each other, a hydrogen atom, a $C_1$-$C_6$ alkyl radical or a $C_1$-$C_6$ mono- or polyhydroxyalkyl radical,
A denotes a linear or branched alkylene radical comprising from 1 to 18 carbon atoms, and optionally from 1 to 9 oxygen atoms, but no hydroxyl group,
m denotes 0 or 1.

A first group of preferred polyols consists of the polyols having the formula above for which m=0, such as 1,2,3-propanetriol (glycerol), propylene glycol (or 1,2-propanediol), pinacol (2,3-dimethyl-2,3-butanediol), 1,2,3-butanetriol, 2,3-butanediol, 1,2-octanediol and sorbitol.

A second group of preferred polyols consists of the polyols having the formula above for which m=1 and R'$_1$, R'$_2$, R'$_3$ and R'$_4$ denote, independently of one another, a hydrogen atom or a $C_1$-$C_6$ alkyl radical, such as polyethylene glycols, in particular those having from 4 to 9 ethylene oxide groups, for instance the products called PEG-6 or PEG-8 (CTFA name).

A third group of preferred polyols consists of the polyols having the formula above for which m=1 and R'$_1$, R'$_2$, R'$_3$ and R'$_4$ denote, independently of one another, a hydrogen atom, a $C_1$-$C_6$ alkyl radical or a $C_1$-$C_6$ mono- or polyhydroxyalkyl radical, and A denotes a linear or branched alkylene radical comprising 1 to 6 carbon atoms, such as 3-methyl-1,3,5-pentanetriol, 1,2,4-butanetriol, 1,5-pentanediol, 2-methyl-1,3-propanediol, 1,3-butanediol, 3-methyl-1,5-pentanediol, neopentyl glycol (2,2-dimethyl-1,3-propanediol), isoprene glycol (3-methyl-1,3-butanediol) and hexylene glycol (2-methyl-2,4-pentanediol), and even more preferably hexylene glycol, propylene glycol, neopentyl glycol and 3-methyl-1,5-pentanediol.

Preferably, the polymers used are liquid at 25° C., 1 atm.

Preferably, the composition according to the invention comprises one or more polyols more particularly chosen from glycerol, propylene glycol, sorbitol, polyethylene glycols, hexylene glycol, and mixtures thereof.

The polyols are preferably present in the composition in an amount ranging from 0.1% to 60% by weight, preferentially from 0.5% to 50% by weight and even better still from 1% to 30% by weight, relative to the total weight of the composition.

Additional Ingredients

The composition according to the invention may also comprise other ingredients commonly used in cosmetic compositions. Such ingredients may be chosen from antioxidants, fragrances, essential oils, preservatives, cosmetic active agents, moisturizers, vitamins, sunscreens, emulsifiers, thickeners, gelling agents, spreading agents, wetting agents, dispersants, antifoams, neutralizing agents, stabilizers, and mixtures thereof. Needless to say, those skilled in the art will take care to select these optional additional ingredients, and/or the amount thereof, such that the advantageous properties of the composition according to the invention are not, or are not substantially, adversely affected by the envisioned addition.

The composition according to the invention may also comprise one or more amphoteric or zwitterionic surfactants.

Said additional amphoteric or zwitterionic surfactants that may be used in the invention may be optionally quaternized secondary or tertiary aliphatic amine derivatives, in which the aliphatic group is a linear or branched chain comprising from 8 to 22 carbon atoms, said amine derivatives containing at least one anionic group, for instance a carboxylate, sulfonate, sulfate, phosphate or phosphonate group.

Mention may be made in particular of ($C_8$-$C_{20}$)alkylbetaines, sulfobetaines, alkyl($C_8$-$C_{20}$)sulfobetaines, ($C_8$-$C_{20}$)alkylamido($C_1$-$C_6$)alkylbetaines, such as cocamidopropylbetaine, and ($C_8$-$C_{20}$)alkylamido($C_1$-$C_6$)alkylsulfobetaines.

Among the optionally quaternized secondary or tertiary aliphatic amine derivatives that may be used, mention may also be made of the products having the following respective structures (A2) and (A3):

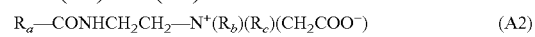   (A2)

in which:

$R_a$ represents a $C_{10}$-$C_{30}$ alkyl or alkenyl group derived from an acid $R_a$COOH preferably present in hydrolyzed coconut oil, or a heptyl, nonyl or undecyl group, $R_b$ represents a β-hydroxyethyl group, and $R_c$ represents a carboxymethyl group;

$$R_a\text{—CONHCH}_2\text{CH}_2\text{—N(B)(B')} \quad (A3)$$

in which:

B represents —CH$_2$CH$_2$OX',

X' represents the —CH$_2$—COOH, CH$_2$—COOZ', —CH$_2$CH$_2$—COOH, or —CH$_2$CH$_2$—COOZ' group, or a hydrogen atom, B' represents —(CH$_2$)$_z$—Y', with z=1 or 2, Y' represents —COOH, —COOZ', or the group —CH$_2$—CHOH—SO$_3$H or CH$_2$—CHOH—SO$_3$Z', Z' represents an ion resulting from an alkali metal or alkaline-earth metal, such as sodium, potassium or magnesium; an ammonium ion; or an ion resulting from an organic amine and in particular from an amino alcohol, such as monoethanolamine, diethanolamine and triethanolamine, monoisopropanolamine, diisopropanolamine or triisopropanolamine, 2-amino-2-methyl-1-propanol, 2-amino-2-methyl-1,3-propanediol and tris(hydroxymethyl)aminomethane, $R_a'$ represents a $C_{10}$-$C_{30}$ alkyl or alkenyl group of an acid $R_a'$COOH preferably present in hydrolyzed linseed oil or coconut oil, an alkyl group, in particular a $C_{17}$ alkyl group, and its iso form, or an unsaturated $C_{17}$ group.

The compounds corresponding to formula (A3) are preferred. These compounds are also classified in the CTFA dictionary, 5th edition, 1993, under the names disodium cocoamphodiacetate, disodium lauroamphodiacetate, disodium caprylamphodiacetate, disodium caprylamphodiacetate, disodium cocoamphodipropionate, disodium lauroamphodipropionate, disodium caprylamphodipropionate, disodium caprylamphodipropionate, lauroamphodipropionic acid, cocoamphodipropionic acid. By way of example, mention may be made of the cocoamphodiacetate sold by the company Rhodia under the trade name Miranol® C$_2$M Concentrate.

Use may also be made of compounds of formula (A4):

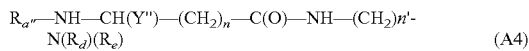

$$R_{a''}\text{—NH—CH(Y'')—(CH}_2)_n\text{—C(O)—NH—(CH}_2)n'\text{—N(R}_d)(R_e) \quad (A4)$$

in which:

$R_{a''}$ represents a $C_{10}$-$C_{30}$ alkyl or alkenyl group of an acid $R_{a''}$—C(O)OH, which is preferably present in hydrolyzed linseed oil or coconut oil;

Y'' represents the group —C(O)OH, —C(O)OZ'', —CH$_2$—CH(OH)—SO$_3$H or the group —CH$_2$—CH(OH)—SO$_3$—Z'', with Z'' representing a cationic counterion resulting from an alkali metal or alkaline-earth metal, such as sodium, an ammonium ion or an ion resulting from an organic amine;

$R_d$ and $R_e$ represent, independently of each other, a $C_1$-$C_4$ alkyl or hydroxyalkyl radical; and n and n' denote, independently of each other, an integer ranging from 1 to 3.

Mention may in particular be made of the compound classified in the CTFA dictionary under the name sodium diethylaminopropyl cocoaspartamide and sold by the company Chimex under the name Chimexane HB.

Preferably, the amphoteric or zwitterionic surfactants are chosen from ($C_8$-$C_{20}$)alkyl betaines, ($C_8$-$C_{20}$)alkylamido($C_1$-$C_6$)alkyl betaines and ($C_8$-$C_{20}$)alkylamphodiacetates, and also the sodium salt of diethylaminopropyl laurylaminosuccinamate, and mixtures thereof.

Preferentially, the amphoteric or zwitterionic surfactants are chosen, alone or as a mixture, from cocoylamidopropyl betaine, cocoyl betaine and cocoamphodiacetate.

The composition according to the invention may comprise said amphoteric or zwitterionic surfactant(s) in an amount preferably between 0.1% and 30% by weight, in particular between 1% and 20% by weight, relative to the total weight of the composition.

The composition may also comprise one or more salts which are soluble in said composition, said salts being other than a surfactant.

Said salts are preferably water-soluble and have a solubility in water greater than 5% at 25° C., 1 atm. Preferentially, use will be made of a salt of an alkali metal or an alkaline-earth metal, even more preferentially an inorganic salt. Mention may in particular be made of sodium chloride and magnesium chloride.

Preferably, said water-soluble salts are present in the composition of the invention in a concentration ranging from 0.01% to 20% by weight, better still from 0.1% to 10% by weight, relative to the total weight of the composition.

The composition according to the invention is not anhydrous; it is aqueous, which means that it comprises at least 20% by weight of water; preferably, it comprises water in a concentration ranging from 20% to 80% by weight, in particular from 35% to 75% by weight, or even from 40% to 70% by weight, better still from 45% to 65% by weight, even better still from 50% to 65% by weight, relative to the total weight of the composition.

The composition may also additionally comprise one or more organic solvents that are liquid at 25° C., 1 atm, other than the abovementioned compounds, in particular polyols and/or conditioners, such as $C_1$-$C_7$ alcohols, in particular aliphatic or aromatic $C_1$-$C_7$ monoalcohols, such as ethanol, isopropanol, benzyl alcohol and mixtures thereof.

Preferably, the composition has a pH of between 2 and 11, in particular 3 to 9, preferentially between 5 and 7.

The compositions according to the invention can be prepared by mixing the various ingredients at ambient temperature (25° C.), or else by mixing under hot conditions, at a temperature between 25 and 80° C., an aqueous phase and a fatty phase, in particular in the case of the presence of solid fatty substances.

The cosmetic composition according to the invention in particular finds a particularly advantageous application in the field of hair hygiene, in particular for caring for, cleaning and/or conditioning keratin materials, in particular cleaning the hair.

The hair compositions are preferably shampoos, or compositions for preventing hair loss, or which are antiparasitic, antidandruff or antiseborrhoeic.

The cosmetic composition may optionally be rinsed off after having been applied to the keratin materials. It is thus optionally possible to perform rinsing, for example with water, after an optional leave-on time. The cosmetic composition is preferably rinsed off.

A subject of the invention is also a cosmetic treatment method, in particular for caring for, cleaning and/or conditioning in keratin materials, which consists in applying a composition as described above to said keratin materials, and in optionally rinsing, for example with water, after an optional leave-on time. Preferably, rinsing is carried out after an optional leave-on-time.

It is preferably a hair treatment method, for cleaning or washing the hair.

The present invention is illustrated in greater detail in the examples that follow (% AM=active material in the composition).

EXAMPLES 1 and 2

Washing hair compositions comprising the following ingredients (% by weight of commercial raw material) are prepared:

|  | Example 1 | Example 2 |
|---|---|---|
| SODIUM COCOYL ISETHIONATE (HOSTAPON SCI 85) |  | 33 (29% AM) |
| SODIUM COCOYL ISETHIONATE/SODIUM ISETHIONATE (JORDAPON CI from BASF) | 33.58 (28.7% AM) |  |
| Acrylic acid/MAPTAC/acrylamide terpolymer at 20% as an aqueous solution (Merquat 2003) | 0.4 (0.08% AM) |  |
| Hydroxypropylguar trimethylammonium chloride |  | 0.2 |
| Oxyethylenated glycerol (26 OE) | 3.7 | 3.7 |
| Glycol distearate | 6.7% | 6.7% |
| 1,2-Octanediol | 0.3 | 0.3 |
| Fragrance, preservative | Qs | Qs |
| pH agent | Qs for pH 5.5 | Qs for pH 5.5 |
| Water | Qs for 100% | Qs for 100% |

The compositions according to the examples are in the form of flexible solids. These compositions are used for cleaning the hair. During use, good distribution of the product on the head of hair, and also the obtaining of a creamy, smooth and abundant foam, are observed. The compositions rinse off and are eliminated easily.

The composition of example 2 is tested on half a head, in comparison with a standard shampoo, on a panel of 6 individuals.

It is noted that, with the composition according to the invention:
- the distribution of the product and the initiation of foaming are close to those obtained with the standard shampoo;
- the abundance of foam is much greater; the hair is smoother in the foam;
- the rapidity of rinsing is very much greater.

With the composition according to the invention, the manageability of wet hair is improved, the hairs are more individualized and the hair is more tonic. On the dry hair, the hair is more tonic.

For example 2:
- the viscoelastic spectrum (G' and G" as a function of frequency) is plotted for frequencies of between $10^{-2}$ Hz and 100 Hz, at 25° C., under the conditions described in the description; it is observed that there is no crossover point of the two curves;
- the threshold stress at 25° C. is also measured, and it is determined that this stress is greater than 100 Pa;
- the penetration force is measured and is 427 g.

EXAMPLES 3 to 6

Washing hair compositions comprising the following ingredients (% by weight of commercial raw material) are prepared:

|  | Example 3 | Example 4 | Example 5 | Example 6 |
|---|---|---|---|---|
| SODIUM COCOYL ISETHIONATE (HOSTAPON SCI 85) | 33 (29% AM) | 33 (29% AM) | 33 (29% AM) | 33 (29% AM) |
| Kaolin |  |  |  | 3 |
| PDMS (500 000 cst; MW = 250 000) |  | 2 | 2 | 2 |
| Polydimethyldiallylammonium chloride at 40% in water (Polyquaternium 6) | 1 (0.4% AM) |  |  |  |
| Amodimethicone containing 57.5% AM (Xiameter MEM-8299 Emulsion from Dow Corning) | 2% AM |  |  |  |
| Glycerol | 15 | 20 | 20 | 20 |
| Glycol distearate | 6.7% | 6.7% | 6.7% | 6.7% |
| NaCl | 3.5 | 3.5 | 3.5 | 3.5 |
| Zinc pyrithione (at 48% in water) |  |  | 2.8% (1% AM) |  |
| Sorbitan monolaurate 4 OE |  | 3% |  |  |
| 1,2-Octanediol | 0.2 |  |  |  |
| Fragrance, preservative | Qs | Qs | Qs | Qs |
| pH agent | Qs for pH 5.5 | Qs for pH 5.5 | Qs for pH 5.5 | Qs for pH 5.5 |
| Water | Qs for 100% | Qs for 100% | Qs for 100% | Qs for 100% |

Compositions 3 to 6 are in the form of flexible solids.

These compositions are used for cleaning the hair. During use, good distribution of the product on the head of hair, and also the obtaining of a creamy, smooth and abundant foam, are observed. The compositions rinse off and are eliminated easily.

The invention claimed is:

1. An aqueous cosmetic hair composition in flexible solid form, comprising:
    at least one anionic surfactant wherein at least one anionic surfactant is chosen from acyl isethionates represented by the following formula:

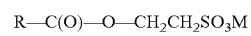
    R—C(O)—O—CH$_2$CH$_2$SO$_3$M wherein:
    R—C(O) is an acyl group comprising from 6 to 16 carbon atoms, and
    M denotes a cosmetically acceptable counterion,
    at least one type of solid full particles chosen from silicas, clays, pigments, pearlescent agents, or mixtures thereof, wherein the total amount of solid particles ranges from 6.7% to 15% by weight, relative to the total weight of the composition, and
    water in an amount of 35% to 80% by weight;
    wherein the total amount of anionic surfactant ranges from 25% to 70% by weight, relative to the total weight of the composition;
    wherein the total amount of acyl isethionates ranges from 12% to 35% by weight, relative to the total weight of the composition, and
    wherein the composition has a threshold stress at 25° C. of greater than or equal to about 100 Pa.

2. The composition according to claim 1, wherein the composition has a penetration force at 25° C. of greater than or equal to about 210 g.

3. The composition according to claim 1, wherein the composition has a viscoelastic spectrum at 25° C., measured between $10^{-2}$ Hz and 100 Hz, such that there is no crossover point between the curves G' and G", G' always being strictly greater than G".

4. The composition according to claim 1, wherein
M denotes a cosmetically acceptable counterion chosen from cocoyl isethionates, lauroyl isethionates, or mixtures thereof.

5. The composition according to claim 1, further comprising at least one additional anionic surfactant chosen from:
- $C_6$-$C_{24}$ alkyl sulfates or $C_{12}$-$C_{20}$ alkyl sulfates;
- $C_6$-$C_{24}$ alkyl ether sulfates, $C_{12}$-$C_{20}$ alkyl ether sulfates, $C_6$-$C_{24}$ alkyl ether sulfates comprising from 2 to 20 ethylene oxide units, or $C_{12}$-$C_{20}$ alkyl ether sulfates comprising from 2 to 20 ethylene oxide units;
- $C_6$-$C_{24}$ acyl glutamates, $C_{12}$-$C_{20}$ acyl glutamates, or glutamates;
- $C_6$-$C_{24}$ acylsarcosinates, $C_{12}$-$C_{20}$ acylsarcosinates, or palmitoylsarcosinates;
- $C_6$-$C_{24}$ acyl lactylates, $C_{12}$-$C_{20}$ acyl lactylates, or behenoyl lactylates;
- ($C_6$-$C_{24}$)alkyl ether carboxylates, or ($C_{12}$-$C_{20}$)alkyl ether carboxylates; or
- $C_6$-$C_{24}$ alkylsulfosuccinates, $C_{12}$-$C_{20}$ alkylsulfosuccinates, or laurylsulfosuccinates.

6. The composition according to claim 1, wherein the total amount of anionic surfactant ranges from 25% to 65% by weight, relative to the total weight of the composition.

7. The composition according to claim 1, wherein the at least one type of solid full particles is chosen from:
- kaolin; or
- organic or inorganic colored pigments, or uncolored pearlescent agents.

8. The composition according to claim 1, further comprising at least one conditioning agent chosen from cationic surfactants, fatty esters other than triglycerides, fatty alcohols, vegetable oils, $C_6$-$C_{16}$ liquid hydrocarbons, hydrocarbons having more than 16 carbon atoms, ceramides, vegetable or animal waxes; non-silicone cationic polymers, non-silicone amphoteric polymers, or silicones.

9. The composition according to claim 8, wherein the total amount of conditioning agent ranges from 0.001% to 20% by weight, relative to the total weight of the composition.

10. The composition according to claim 1, further comprising at least one polyol represented by the following formula:

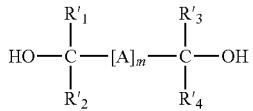

wherein:
R'$_1$, R'$_2$, R'$_3$ and R'$_4$ are chosen, independently of each other, a hydrogen atom, a $C_1$-$C_6$ alkyl radical or a $C_1$-$C_6$ mono- or polyhydroxyalkyl radical,
A represents a linear or branched alkylene radical comprising from 1 to 18 carbon atoms, and optionally from 1 to 9 oxygen atoms, wherein A does not include a hydroxyl group,
m denotes 0 or 1.

11. The composition according to claim 10, wherein the total amount of polyol ranges from 0.1% to 60% by weight, relative to the total weight of the composition.

12. The composition according to claim 1, further comprising at least one non-particulate antidandruff agent chosen from:
- 1-hydroxy-2-pyrolidone derivatives;
- 2,2'-dithiobis(pyridine N-oxide);
- trihalocarbamides;
- triclosan;
- azole compounds;
- antifungal polymers;
- extracts of at least one non-photosynthetic, non-fruiting filamentous bacteria;
- ellagic acid, ethers of ellagic acid, salts of ellagic acid, salts of ethers of ellagic acid, or ellagic acid tannins;
- allantoin, coal or wood tars and derivatives thereof, undecylenic acid, fumaric acid, allylamines, or terbinafine.

13. The composition according to claim 12, wherein the total amount of non-particulate antidandruff agent ranges from 0.01% to 10% by weight, relative to the total weight of the composition.

14. The composition according to claim 1, comprising water in an amount ranging from 40% to 80% by weight, relative to the total weight of the composition.

15. A cosmetic hair treatment method for caring for, cleaning, and/or conditioning keratin materials, the method comprising:
applying to the keratin materials a composition comprising:
at least one anionic surfactant wherein at least one anionic
surfactant is chosen from acyl isethionates represented by the
following formula:

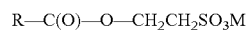

wherein:
R—C(O) is an acyl group comprising from 6 to 16 carbon atoms, and
M denotes a cosmetically acceptable counterion,
at least one type of solid full particles chosen from silicas, clays, pigments, pearlescent agents, or mixtures thereof, wherein the total amount of solid particles ranges from 6.7% to 15% by weight, relative to the total weight of the composition, and
water in an amount of 35% to 80% by weight;
wherein the total amount of anionic surfactant ranges from 25% to 70% by weight, relative to the total weight of the composition; and
optionally rinsing after an optional leave-on time;
wherein the total amount of acyl isethionates ranges from 12% to 35% by weight, relative to the total weight of the composition, and
wherein the composition has a threshold stress at 25° C. of greater than or equal to about 100 Pa.

* * * * *